(12) United States Patent
June et al.

(10) Patent No.: US 12,404,314 B2
(45) Date of Patent: Sep. 2, 2025

(54) SWITCH COSTIMULATORY RECEPTORS

(71) Applicant: The Trustees of the University of Pennsylvania, Philadelphia, PA (US)

(72) Inventors: Carl H. June, Merion Station, PA (US); Yangbing Zhao, Lumberton, NJ (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1397 days.

(21) Appl. No.: 16/408,923

(22) Filed: May 10, 2019

(65) Prior Publication Data

US 2019/0345219 A1 Nov. 14, 2019

Related U.S. Application Data

(62) Division of application No. 14/232,557, filed as application No. PCT/US2012/048543 on Jul. 27, 2012, now Pat. No. 10,981,969.

(60) Provisional application No. 61/513,259, filed on Jul. 29, 2011.

(51) Int. Cl.
| | | |
|---|---|---|
| A61K 40/30 | (2025.01) | |
| A61K 38/17 | (2006.01) | |
| A61K 40/11 | (2025.01) | |
| A61K 40/31 | (2025.01) | |
| A61K 40/42 | (2025.01) | |
| C07K 14/705 | (2006.01) | |
| C07K 14/725 | (2006.01) | |
| A61K 38/00 | (2006.01) | |
| A61K 48/00 | (2006.01) | |

(52) U.S. Cl.
CPC .... *C07K 14/70503* (2013.01); *A61K 38/1774* (2013.01); *A61K 40/11* (2025.01); *A61K 40/31* (2025.01); *A61K 40/421* (2025.01); *A61K 40/4211* (2025.01); *C07K 14/7051* (2013.01); *C07K 14/70521* (2013.01); *A61K 38/00* (2013.01); *A61K 48/005* (2013.01); *A61K 2239/17* (2023.05); *C07K 2319/00* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 5,199,942 A | 4/1993 | Gillis et al. | |
| 5,350,674 A | 9/1994 | Boenisch et al. | |
| 5,359,046 A * | 10/1994 | Capon | C07K 14/70514 |
| | | | 435/235.1 |
| 5,585,362 A | 12/1996 | Wilson et al. | |
| 5,686,281 A | 11/1997 | Roberts | |
| 7,101,550 B2 | 9/2006 | Wood et al. | |
| 7,285,522 B2 | 10/2007 | Van et al. | |
| 2003/0216546 A1 | 11/2003 | Tykocinski et al. | |
| 2006/0247191 A1 | 11/2006 | Finney et al. | |
| 2010/0316646 A1 | 12/2010 | Gao et al. | |
| 2011/0171220 A1 | 7/2011 | Davis | |
| 2011/0262457 A1* | 10/2011 | Weiner | A61P 31/10 |
| | | | 424/234.1 |

FOREIGN PATENT DOCUMENTS

| | | |
|---|---|---|
| CN | 101355965 | 1/2009 |
| JP | 2006518984 | 8/2006 |
| JP | 6334398 | 5/2018 |
| WO | 0129058 A1 | 4/2001 |
| WO | 0196584 A2 | 12/2001 |
| WO | 2004039840 A1 | 5/2004 |
| WO | 2005044996 A2 | 5/2005 |
| WO | 2010025177 A1 | 3/2010 |
| WO | 2011090762 A1 | 7/2011 |

OTHER PUBLICATIONS

Murphy et al. Induction by Antigen of Intrathymic Apoptosis of CD4+CD8+ TCRIo Thymocytes in Vivo (Science, 1990, 250:1720-1723) (Year: 1990).*
Zamoyska et al. Inability of CD8a' polypeptides to associate with p56kk correlates with impaired function in vitro and lack of expression in vivo (Nature, 1989, 342:278-281) (Year: 1989).*
Bauer et al. Identification of H-2Kb binding and immunogenic peptides from human papilloma virus tumour antigens E6 and E7 (Scand J Immuno, 1995, 42:317-323) (Year: 1995).*
European Patent Application No. 19162250.5—Extended European Search Report dated Sep. 5, 2019.
Japanese Patent Application No. 2018-084610—Notice of Reasons for Rejection dispatched Oct. 30, 2019.
Watanabe, et al., "BTLA is a lymphocyte inhibitory receptor with similariities to CTLA-4 and PD-1.", 2003, Nature Immunology 4(7):670-679.
Barrett David M et al, "Pre-clinical model of eradication of B cell leukemia with lentiviral transduced anti-CD19 chimeric immunoreceptor-modified T cells", 101st Annual Meeting of the American-Association-For-Cancer-Research; Washington, DC, USA; Apr. 17-21, 2010, (Apr. 2010), Proceedings of the American Association for Cancer Research Annual Meeting.
Japanese Patent Application No. 2018-084610—Notice of Reasons for Rejection dispatched Mar. 27, 2019.
Australian Patent Application No. 2015590342—Examination Report No. 1, issued Jun. 30, 2016.
Chinese Patent Application No. 201280041432.6—Fifth Office Action dated May 14, 2018.

(Continued)

*Primary Examiner* — Arthur S Leonard
(74) *Attorney, Agent, or Firm* — Saul Ewing, LLP; Kathryn Doyle; Alireza Behrooz

(57) ABSTRACT

The present invention relates generally to a fusion protein that when displayed on a cell can convert a negative signal into a positive signal in the cell. The fusion protein is a chimeric protein in that the protein comprises at least two domains, wherein the first domain is a polypeptide that is associated with a negative signal and the second domain is a polypeptide that is associated with a positive signal. Thus, the invention encompasses switch receptors that are able to switch negative signals to positive signals for enhancement of an immune response.

15 Claims, 23 Drawing Sheets

Specification includes a Sequence Listing.

(56) References Cited

OTHER PUBLICATIONS

Chinese Patent Application No. 201280041432.6—Office Action issued Dec. 31, 2015.
Chinese Patent Application No. 201280041432.6—Third Office Action issued Jan. 19, 2017.
Chinese Patent Application No. 2012800414326—Decision of Rejection dated Oct. 24, 2018.
Chinese Patent Application No. 2012800414326—Office Action dated Oct. 9, 2017.
Colombia Patent Application No. 14-12252—Office Action issued May 10, 2016 (no available translation).
Colombia Patent Application No. 14-12252—Office Action issued Sep. 2015 (no available translation).
Eurasian Region Patent Application No. 201490364/28—Office Action issued Jan. 2016.
European Patent Application No. 12820516.8—Office Action issued Jul. 14, 2016.
European Patent Application No. 12820516.8—Official Communication pursuant to Article 94(3) EPC dated Sep. 14, 2017.
European Search Report for European Patent Application No. 12820516.8 dated Mar. 30, 2015.
International search report for PCT/US12/48543 dated Oct. 16, 2012.
Japanese Patent Application No. 2014-523064—Notice of Reasons for Rejection issued May 23, 2016.
Japanese Patent Application No. 2014-523064—Office Action dated May 11, 2017.
Singapore Patent Application No. 2014004170—Written Opinion issued May 23, 2016.
Chinese Patent Application No. 201280041432.6—Second Office Action issued Jul. 19, 2016. ,2016.
Beck, et al.,Enterocolitis in Patients with Cancer after Antibody Blockade of Cytotoxic T-Lymphocyte-Associated Antigen 4, 2006, J Clin Oncol 24:2283-9.
Bierer, et al.,Cyclosporin A and FK506: molecular mechanisms of immunosuppression and probes for transplantation biology, Curr. Opin. Immun. 5:763-773, 1993.
Bird, et al.,Single-chain antigen-binding proteins, 1988, Science 242:423-426.
Blansfield, et al.,Cytotoxic T-Lymphocyte-Associated antigen-4 Blockage Can Induce Autoimmune Hypophysitis in Patients with Metastatic Melanoma and Renal Cancer, 2005, J Immunother 28:593-8.
Carpenito, et al.,Control of large, established tumor xenografts with genetically retargeted human T cells containing CD28 and CD137 domains, 2009, PNAS 106(9):3360-3365.
Cheever, et al.,Twelve immunotherapy drugs that could cure cancers, 2008, Immunol Rev 222:357-68 (Abstract).
Chemnitz, et al.,B and T Lymphocyte Attenuator-Mediated Signal Transduction Provides a Potent Inhibitory Signal to Primary Human CD4 T Cells that can be Initiated by Multiple Phosphotyrosine Motifs., 2006, J Immunol 176:6603-14.
Dennehy, et al.,Cutting Edge: Monovalency of CD28 Maintains the Antigen Dependence of T Cell Costimulatory Responses, 2006, J Immunol 176:5725-5729.
Derré, et al.,BTLA mediates inhibition of human tumor-specific CD8+ T cells that can be partially reversed by vaccination, 2010, J Clin Invest 120:157-67.
Dougan, et al.,Immune therapy for cancer, 2009, Annual Review of Immunology 27:83-117 (Abstract).
Finney, et al.,Activation of Resting Human Primary T cells with Chimeric Receptors: Costimulation from CD28, Indcible Costimulatory, CD134 and CD137 in Series with Signals from the TCRz Chain, J Immunol 2004, 174:104-113.
Garaude, et al.,ICOStomizing immunotherapies with T(H)17, 2010, Sci Transl Med 2(55):55ps2 (Abstract).
Henderson, et al.,"Comparison of the effects of FK-506, cyclosporine A and rapamycin on IL-2 production.", Immun. 73:316-321, 1991.

Huston, et al.,"Protein engineering of antibody binding sites: Recovery of specific activity in an anti-digoxin single-chain Fv analogue produced in *Escherichia coli*.", 1988, Proc. Natl. Acad. Sci. USA 85:5879-5883.
June, et al.,Engineering lymphocyte subsets: tools, trials and tribulations, Nat Rev Immunol 9:704, 2009.
Lajaunias, et al.,Constitutive repressor activity of CD33 on human moncytes requires sialic acid recognition and phosphoinositide 3-kinase-mediated intracellular signaling., Eur J Immunol. 2005, 35:243-251.
Laport, et al.,Adoptive transfer of costimulated T cells induces lymphocytosis in patients with relapsed/refractory non-Hodgkin lymphoma following CD34+-selected hematopoietic cell transplantation, 2003, Blood 102:2004-2013.
Levine, et al.,Gene transfer in humans using a conditionally replicating lentiviral vector, 2006, Proc Natl Acad Sci U S A 103:17372-17377.
Liu, et al.,Calcineurin is a Common Target of Cyclophilin-Cyclosporin A and FKBP-FK506 Complexes, Cell 66:807-815, 1991.
Martin-Orozco, et al.,Th17 cells promote cytotoxic T cell activation in tumor immunity, 2009, Immunity 31:787-98.
Moon, et al., May 2014, 17th Annual Meeting of the American Society of Gene and Cell Therapy "APD1-CD28 "Switch Receptor" Is able to augment Mesothelin-Directed Chimeric Antigen Receptor T Cell Therapy in a Resistant In Vivo Model of Human Tumor."
Mumtaz, et al.,Design of liposomes for circumventing the reticuloendothelial cells, 1991 Glycobiology 5: 505-10.
Parry, et al.,CTLA-4 and PD-1 Recptors Inhibit T-cell Activation by Distinct Mechanisms, Mol Cell Biol. Nov. 2005;25(21):9543-9553.
Paulos, et al.,Putting the brakes on BTLA in T cell-mediated cancer immunotherapy, 2010 J Clin Invest 120 (1):76-80.
Paulos, et al.,The inducible costimulatory (ICOS) is critical for the development of human T(H)17 cells, 2010, Science Translational Medicine 2:55-78 (Abstract).
Prosser, et al.,Tumor PD-L1 co-stimulates primary human CD8(+) cytotoxic T cells modified to express a PD1: CD28 chimeric receptor, 2012, Molecular Immunology 51(3):263-272 (Abstract).
Riley, et al.,The CD28 family: a T-cell rheostat for therapeutic control of T-cell activation, 2005, Blood 105:13-21.
Ryo, et al.,Regulation of immune response by T cell co-signaling, Japanese Journal of Clinical Immunology, 2005, vol. 28, No. 1, pp. 21-32 (with partial English translation).
Schroers, et al.,Gene transfer into human T lymphocytes and natural killer cells by AD5/F35 chimeric adenoviral vectors, Exp Hematol 32:536, 2004 (Abstract).
Ui-Tei, et al.,Sensitive assay of RNA interference in *Drosophila* and Chinese hamster cultured cells using firefly luciferase gene as target., 2000 FEBS Letters 479: 79-82.
Wherry, et al.,T Cell Exhaustion, Nature Immunology ,2011 ,492-498.
Yin, et al.,Short cytoplasmic SDYMNM segment of CD28 is sufficient to convert CTLA-4 to a positive signaling receptor., 2003, Journal of Leukocyte Biology 73:178-182.
Zhao, et al.,Multiple injections of electroporated autologous T cells expressing a chimeric antigen receptor mediate regression of human disseminated tumor, Cancer Res 70:9062, 2010.
Berry, L. J. et al., "Adoptive immunotherapy for cancer: the next generation of gene-engineered immune cells," Tissue Antigens (2009) 74: 277-289.
Bochner, B., "Siglec-8 on human eosinophils and mast cells, and Siglec-F on murine eosinophils, are functionally related inhibitory receptors," Clin. Exp. Allergy (2009), 39(3): 317-324.
Boyington J. et al., "Structure of CD94 reveals a novel C-type lectin fold: Implications for the NK cell-associated CD94/NKG2 receptors," Immunity (1999), 10: 75-82.
Carter L. et al., "PD-1:PD-L inhibitory pathway affects both CD4(+) and CD8(+) T cells and is overcome by IL-2," Eur. J. Immunol. (2002), 32: 634-643.
Chang, C. et al., "Molecular characterization of human CD94: a type II membrane glycoprotein related to the C-type lectin superfamily," Eur. J. Immunol. (1995), 25: 2433-2437.

(56) References Cited

OTHER PUBLICATIONS

Chou, K. and Elrod D., Prediction of membrane protein types and subcellular locations, Proteins: Structure, Function and Genetics, (1999), 34: 137-153.

Davis D. and Maher J., "Adoptive T-cell immunotherapy of cancer using chimeric antigen receptor-grafted T cells," Arch. Immunol. Ther. Exp. (2010), 58: 165-178.

Kellar, D. et al., "CD56-Specific T Cells Can Distinguish between Allogeneic and Autologous CD56+ Targets," Abstract 500, Molecular Therapy (May 2011), 19, Supplement 1: S192-S193.

Li, Z. et al., "Paradoxical roles of IL-4 in tumor immunity," Cellular & Molecular Immunology (2009), 6(6): 415-422.

Liu, X. et al., "A Chimeric Switch-Receptor Targeting PD1 Augments the Efficacy of Second-Generation CAR T Cells in Advanced Solid Tumors," Cancer Res. (2016), 76(6): 1578-1590.

Ngo, M. et al., "Ex vivo gene transfer for improved adoptive immunotherapy of cancer," Human Molecular Genetics (Mar. 17, 2011), 20(1):R93-R99.

Olver, S. et al., "The duplicitous effects of interleukin 4 on tumour immunity: how can the same cytokine improve or impair control of tumour growth?," Tissue Antigens (2007), 69: 293-298.

Prosser, M. et al., "Mechanistic Studies of PD-1 Signaling in the Conversion of Effector T Cells to Functional Exhaustion," Abstract 565, Molecular Therapy (2009), 17, Supplement 1: S216.

Prosser, M. et al., "Primary Human cos+ T Cells Engineered To Express a PD1-CD28 Chimeric Receptor Are Co-Stimulated through the Exploitation of Tumor Expressed PD-L 1," Abstract 49, Molecular Therapy (May 2011), 19, Supplement 1: S192.

Prosser, M. et al.,Tumor PD-L1 co-stimulates primary human CD8(+) cytotoxic T cells modified to express a PD1: CD28 chimeric receptor, 2012, Molecular Immunology 51(3):263-272.

Prosser, M., "Development of Genetic Engineering Platforms to Protect T Cells Against Functional Exhaustion, Dissertation from 2011: Development of Genetic Engineering Platforms to Protect T Cells Against Functional Exhaustion," UMI No. 3548076.

Ramos C. and Dotti G., "Chimeric Antigen Receptor (CAR)-Engineered Lymphocytes for Cancer Therapy," Expert Opinion on Biological Therapy (Apr. 4, 2011) 11(7): 855-873.

Riley J. and June C., "The CD28 family: a T-cell rheostat for therapeutic control of T-cell activation," Blood (2005), 105 (1): 13-21.

Sadelain, M., "T-cell engineering for cancer immunotherapy," The Cancer Journal (2009), 15(6): 451-455.

Wilkie, S. et al., "Selective expansion of chimeric antigen receptor-targeted T-cells with potent effector function using interleukin-4," J Biol Chem. Aug. 13, 2010;285(33):25538-44.

\* cited by examiner

| Group | Treatment | Co-culture | Cytokines |
|---|---|---|---|
| 1 | BTLA-BTM-ICOS+CD19z | K562CD19-HVEM | Th17 cytokine cocktail |
| 2 | BTLA-BTM-ICOS+CD19z | K562CD19-HVEM | Th17 cytokine cocktail |
| 3 | BTLA-BTM-ICOS | HVEM-Fc/OKT3 | Th17 cytokine cocktail |
| 4 | BTLA-BTM-CD28 +CD19z | K562CD19-HVEM | Th17 cytokine cocktail |
| 5 | CD3/ICOS beads | No | Th17 cytokine cocktail |
| 6 | CD3/CD28 beads | No | Th17 cytokine cocktail |

Donor ND 365; Fresh CD4+ Cells
Th17 cytokine cocktail
- IL-1β  10ng/ml
- IL-6   10ng/ml
- IL-23  20ng/ml
- Anti-IL-4 10μg/ml
- Anti-IFNγ 10μl/ml
- IL-2   50u/ml (start day5)

Figure 3A

SEQUENCE LISTING

```
<160> NUMBER OF SEQ ID NOS: 12

<210> SEQ ID NO 1
<211> LENGTH: 870
<212> TYPE: DNA
<213> ORGANISM: Artificial Sequence
<220> FEATURE:
<223> OTHER INFORMATION: Chemically synthesized

<400> SEQUENCE: 1
atgaagacat tgcctgccat gcttggaact gggaaattat tttgggtctt cttcttaatc      60
ccatatctgg acatctggaa catccatggg aaagaatcat gtgatgtaca gctttatata     120
aagagacaat ctgaacactc catcttagca ggagatccct ttgaactaga atgccctgtg     180
aaatactgtg ctaacaggcc tcatgtgact tggtgcaagc tcaatggaac aacatgtgta     240
aaacttgaag atagacaaac aagttggaag gaagagaaga catttcatt tttcattcta      300 cattttgaac cagtgcttcc taatgacaat gggtcatacc gctgttctgc aaattttcag     360
tctaatctca ttgaaagcca ctcaacaact ctttatgtga cagatgtaaa aagtgcctca     420
gaacgaccct ccaaggacga aatggcaagc agaccctggc tcctgtatag tttacttcct     480
ttggggggat tgcctctact catcactacc tgtttctgcc tgttctgctg cctgagaagg     540
caccaaggaa agcaaaatga actctctgac acagcaggaa gggaaattaa cctggttgat     600
gctcacctta agagtgagca acagaagca agcaccaggc aaaattccca agtactgcta     660
tcagaaactg gaatttatga taatgaccct gacctttgtt tcaggatgca ggaagggtct     720
gaagtttatt ctaatccatg cctggaagaa aacaaaccag gcattgttta tgcttccctg     780
aaccattctg tcattggacc gaactcaaga ctggcaagaa atgtaaaaga agcaccaaca     840
gaatatgcat ccatatgtgt gaggagttaa                                      870

<210> SEQ ID NO 2
<211> LENGTH: 685
<212> TYPE: DNA
<213> ORGANISM: Artificial Sequence
<220> FEATURE:
<223> OTHER INFORMATION: Chemically synthesized

<400> SEQUENCE: 2
aagcttgccg ccatgaagac attgcctgcc atgcttggaa ctgggaaatt attttgggtc      60
ttcttcttaa tcccatatct ggacatctgg aacatccatg ggaaagaatc atgtgatgta     120
cagctttata taaagagaca atctgaacac tccatcttag caggagatcc ctttgaacta     180
gaatgccctg tgaaatactg tgctaacagg cctcatgtga cttggtgcaa gctcaatgga     240
acaacatgtg taaaacttga agatagacaa acaagttgga aggaagagaa gaacatttca     300
```

```
ttttcattc tacattttga accagtgctt cctaatgaca atgggtcata ccgctgttct      360
gcaaattttc agtctaatct cattgaaagc cactcaacaa ctctttatgt gacagatgta      420
aaaagtgcct cagaacgacc ctccaaggac gaaatggcaa gcagaccctg gctcctgtat      480
agtttacttc ctttgggggg attgcctcta ctcatcacta cctgtttctg cctgttctgc      540
tgcctggagg agtaagagga gcaggctcct gcacagtgac tacatgaaca tgactccccg      600
ccgcccgggg cccacccgca agcattacca gccctatgcc ccaccacgcg acttcgcagc      660
ctatcgctcc tgataagcgg ccgca                                           685
```

<210> SEQ ID NO 3  
<211> LENGTH: 701  
<212> TYPE: DNA  
<213> ORGANISM: Artificial Sequence  
<220> FEATURE:  
<223> OTHER INFORMATION: Chemically synthesized

<400> SEQUENCE: 3

```
aagcttgccg ccatgaagac attgcctgcc atgcttggaa ctgggaaatt attttgggtc       60
ttcttcttaa tcccatatct ggacatctgg aacatccatg ggaaagaatc atgtgatgta      120
cagctttata taagagacaa atctgaacac tccatcttag caggagatcc ctttgaacta      180
gaatgccctg tgaaatactg tgctaacagg cctcatgtga cttggtgcaa gctcaatgga      240
acaacatgtg taaaacttga agatagacaa acaagttgga aggaagagaa gaacatttca      300 ttttcattc tacattttga accagtgctt cctaatgaca atgggtcata ccgctgttct       360
gcaaattttc agtctaatct cattgaaagc cactcaacaa ctctttatgt gacagatgta      420
aaaagtgcct cagaacgacc ctccaaggac gaaatggcaa gcagaccctg gctcctgtat      480
agtttacttc ctttgggggg attgcctcta ctcatcacta cctgtttctg cctgttctgc      540
tgcctggaag gaaatataga tcaaacaaag gagaaagtcc tgtggagcct gcagagcctt      600
gtcgttacag ctgccccagg gaggaggagg gcagcaccat ccccatccag gaggattacc      660
gaaaaccgga gcctgcctgc tcccctgat aagcggccgc a                          701
```

<210> SEQ ID NO 4  
<211> LENGTH: 685  
<212> TYPE: DNA  
<213> ORGANISM: Artificial Sequence  
<220> FEATURE:  
<223> OTHER INFORMATION: Chemically synthesized

<400> SEQUENCE: 4

```
aagcttgccg ccatgaagac attgcctgcc atgcttggaa ctgggaaatt attttgggtc       60
ttcttcttaa tcccatatct ggacatctgg aacatccatg ggaaagaatc atgtgatgta      120
cagctttata taagagacaa atctgaacac tccatcttag caggagatcc ctttgaacta      180
gaatgccctg tgaaatactg tgctaacagg cctcatgtga cttggtgcaa gctcaatgga      240
acaacatgtg taaaacttga agatagacaa acaagttgga aggaagagaa gaacatttca      300 ttttcattc tacattttga accagtgctt cctaatgaca atgggtcata ccgctgttct       360
gcaaattttc agtctaatct cattgaaagc cactcaacaa ctctttatgt gacagatgta      420
aaaagtgcct cagaacgacc ctccaaggac gaaatggcaa gcagaccctg gctcctgtat      480
agtttctggt tacccatagg atgtgcagcc tttgttgtag tctgcatttt gggatgcata      540
cttattgagg agtaagagga gcaggctcct gcacagtgac tacatgaaca tgactccccg      600
```

```
ccgccccggg cccacccgca agcattacca gccctatgcc ccaccacgcg acttcgcagc    660
ctatcgctcc tgataagcgg ccgca                                         685
```

<210> SEQ ID NO 5
<211> LENGTH: 701
<212> TYPE: DNA
<213> ORGANISM: Artificial Sequence
<220> FEATURE:
<223> OTHER INFORMATION: Chemically synthesized

<400> SEQUENCE: 5

```
aagcttgccg ccatgaagac attgcctgcc atgcttggaa ctgggaaatt attttgggtc    60
ttcttcttaa tcccatatct ggacatctgg aacatccatg ggaagaatc atgtgatgta    120 cagctttata taaagagaca atctgaacac tccatcttag caggagatcc ctttgaacta    180
gaatgccctg tgaaatactg tgctaacagg cctcatgtga cttggtgcaa gctcaatgga    240
acaacatgtg taaaacttga agatagacaa acaagttgga aggaagagaa gaacatttca    300
tttttcattc tacattttga accagtgctt cctaatgaca atgggtcata ccgctgttct    360
gcaaattttc agtctaatct cattgaaagc cactcaacaa ctctttatgt gacagatgta    420
aaaagtgcct cagaacgacc ctccaaggac gaaatggcaa gcagaccctg gctcctgtat    480
agtttctggt tacccatagg atgtgcagcc tttgttgtag tctgcatttt gggatgcata    540
cttattgaag gaaatataga tcaaacaaag gagaaagtcc tgtggagcct gcagagcctt    600
gtcgttacag ctgccccagg gaggaggagg gcagcaccat ccccatccag gaggattacc    660
gaaaaccgga gcctgcctgc tccccctgat aagcggccgc a                        701
```

<210> SEQ ID NO 6
<211> LENGTH: 672
<212> TYPE: DNA
<213> ORGANISM: Artificial Sequence
<220> FEATURE:
<223> OTHER INFORMATION: Chemically synthesized

<400> SEQUENCE: 6

```
aagcttgccg ccatgaagac attgcctgcc atgcttggaa ctgggaaatt attttgggtc    60
ttcttcttaa tcccatatct ggacatctgg aacatccatg ggaagaatc atgtgatgta    120 cagctttata taaagagaca atctgaacac tccatcttag caggagatcc ctttgaacta    180
gaatgccctg tgaaatactg tgctaacagg cctcatgtga cttggtgcaa gctcaatgga    240
acaacatgtg taaaacttga agatagacaa acaagttgga aggaagagaa gaacatttca    300
tttttcattc tacattttga accagtgctt cctaatgaca atgggtcata ccgctgttct    360
gcaaattttc agtctaatct cattgaaagc cactcaacaa ctctttatgt gacagatgta    420
aaaagtgcct cagaacgacc ctccaaggac gaaatggcaa gcagaccctg gctcctgtat    480
agtttacttc ctttgggggg attgcctcta ctcatcacta cctgtttctg cctgttctgc    540
tgcctgtgtt ggcttacaaa aaagaagtat tcatccagtg tgcacgaccc taacggtgaa    600
tacatgttca tgagagcagt gaacacagcc aaaaaatcta gactcacaga tgtgacccta    660
taagcggccg ca                                                        672
```

<210> SEQ ID NO 7
<211> LENGTH: 1011
<212> TYPE: DNA
<213> ORGANISM: Artificial Sequence
<220> FEATURE:
<223> OTHER INFORMATION: Chemically synthesized

<400> SEQUENCE: 7

```
aagcttgccg ccatgaagac attgcctgcc atgcttggaa ctgggaaatt attttgggtc      60
ttcttcttaa tcccatatct ggacatctgg aacatccatg ggaaagaatc atgtgatgta     120
cagctttata taaagagaca atctgaacac tccatcttag caggagatcc ctttgaacta     180
gaatgccctg tgaaatactg tgctaacagg cctcatgtga cttggtgcaa gctcaatgga     240
acaacatgtg taaaacttga agatagacaa acaagttgga aggaagagaa gaacatttca     300
tttttcattc tacattttga accagtgctt cctaatgaca atgggtcata ccgctgttct     360
gcaaattttc agtctaatct cattgaaagc cactcaacaa ctctttatgt gacagatgta     420
aaaagtgcct cagaacgacc ctccaaggac gaaatggcaa gcagaccctg ctcctgtat      480
agtttacttc ctttgggggg attgcctcta ctcatcacta cctgtttctg cctgttctgc     540
tgcctgtgtt ggcttacaaa aagaagtat tcatccagtg tgcacgaccc taacggtgaa     600
tacatgttca tgagagcagt gaacacagcc aaaaaatcta gactcacaga tgtgacccta     660
tgcagagtga agttcagcag gagcgcagac gcccccgcgt accagcaggg ccagaaccag     720
ctctataacg agctcaatct aggacgaaga gaggagtacg atgttttgga caagagacgt     780
ggccgggacc ctgagatggg gggaaagccg agaaggaaga acccctcagga aggcctgtac     840
aatgaactgc agaaagataa gatggcggag gcctacagtg agattgggat gaaaggcgag     900
cgccggaggg gcaaggggca cgatggcctt taccagggtc tcagtacagc caccaaggac     960
acctacgacg cccttcacat gcaggccctg cccctcgct aagcggccgc a              1011
```

<210> SEQ ID NO 8
<211> LENGTH: 672
<212> TYPE: DNA
<213> ORGANISM: Artificial Sequence
<220> FEATURE:
<223> OTHER INFORMATION: Chemically synthesized

<400> SEQUENCE: 8

```
aagcttgccg ccatgaagac attgcctgcc atgcttggaa ctgggaaatt attttgggtc      60
ttcttcttaa tcccatatct ggacatctgg aacatccatg ggaaagaatc atgtgatgta     120
cagctttata taaagagaca atctgaacac tccatcttag caggagatcc ctttgaacta     180
gaatgccctg tgaaatactg tgctaacagg cctcatgtga cttggtgcaa gctcaatgga     240
acaacatgtg taaaacttga agatagacaa acaagttgga aggaagagaa gaacatttca     300
tttttcattc tacattttga accagtgctt cctaatgaca atgggtcata ccgctgttct     360
gcaaattttc agtctaatct cattgaaagc cactcaacaa ctctttatgt gacagatgta     420
aaaagtgcct cagaacgacc ctccaaggac gaaatggcaa gcagaccctg ctcctgtat      480
agtttctggt tacccatagg atgtgcagcc tttgttgtag tctgcatttt gggatgcata     540
cttatttgtt ggcttacaaa aagaagtat tcatccagtg tgcacgaccc taacggtgaa     600
tacatgttca tgagagcagt gaacacagcc aaaaaatcta gactcacaga tgtgacccta     660
taagcggccg ca                                                         672
```

<210> SEQ ID NO 9
<211> LENGTH: 1011
<212> TYPE: DNA
<213> ORGANISM: Artificial Sequence
<220> FEATURE:
<223> OTHER INFORMATION: Chemically synthesized

<400> SEQUENCE: 9

```
aagcttgccg ccatgaagac attgcctgcc atgcttggaa ctgggaaatt attttgggtc      60
ttcttcttaa tcccatatct ggacatctgg aacatccatg ggaaagaatc atgtgatgta     120
cagctttata taaagagaca atctgaacac tccatcttag caggagatcc ctttgaacta     180
gaatgccctg tgaaatactg tgctaacagg cctcatgtga cttggtgcaa gctcaatgga     240
acaacatgtg taaaacttga agatagacaa acaagttgga aggaagagaa gaacatttca     300
tttttcattc tacattttga accagtgctt cctaatgaca atgggtcata ccgctgttct     360
gcaaattttc agtctaatct cattgaaagc cactcaacaa ctctttatgt gacagatgta     420
aaaagtgcct cagaacgacc ctccaaggac gaaatggcaa gcagaccctg gctcctgtat     480
agtttacttc ctttgggggg attgcctcta ctcatcacta cctgtttctg cctgttctgc     540
tgcctgtgtt ggcttacaaa aaagaagtat tcatccagtg tgcacgaccc taacggtgaa     600
tacatgttca tgagagcagt gaacacagcc aaaaaatcta gactcacaga tgtgacccta     660
tgcagagtga agttcagcag gagcgcagac gcccccgcgt accagcaggg ccagaaccag     720
ctctataacg agctcaatct aggacgaaga gaggagtacg atgttttgga caagagacgt     780
ggccgggacc ctgagatggg gggaaagccg agaaggaaga accctcagga aggcctgtac     840
aatgaactgc agaaagataa gatggcggag gcctacagtg agattgggat gaaaggcgag     900
cgccggaggg gcaaggggca cgatggcctt taccagggtc tcagtacagc caccaaggac     960
acctacgacg cccttcacat gcaggccctg ccccctcgct aagcggccgc a             1011
```

<210> SEQ ID NO 10
<211> LENGTH: 690
<212> TYPE: DNA
<213> ORGANISM: Artificial Sequence
<220> FEATURE:
<223> OTHER INFORMATION: Chemically synthesized

<400> SEQUENCE: 10

```
atgcagatcc cacaggcgcc ctggccagtc gtctgggcgg tgctacaact gggctggcgg      60
ccaggatggt tcttagactc cccagacagg ccctggaacc ccccaccttt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggcccccc aaggcgcaga tcaaagagag cctgcgggca     420
gagctcaggg tgacagagag aagggcagaa gtgcccacag cccacccccag cccctcaccc     480
aggccagccg gccagttcca aaccctggtg ttctggttac ccataggatg tgcagccttt     540
gttgtagtct gcattttggg atgcatactt atttgttggc ttacaaaaaa gaagtattca     600
tccagtgtgc acgaccctaa cggtgaatac atgttcatga gagcagtgaa cacagccaaa     660
aaatctagac tcacagatgt gaccctataa                                     690
```

<210> SEQ ID NO 11
<211> LENGTH: 717
<212> TYPE: DNA
<213> ORGANISM: Artificial Sequence
<220> FEATURE:
<223> OTHER INFORMATION: Chemically synthesized

<400> SEQUENCE: 11

```
atgcagatcc cacaggcgcc ctggccagtc gtctgggcgg tgctacaact gggctggcgg        60
ccaggatggt tcttagactc cccagacagg ccctggaacc cccccacctt ctccccagcc       120
ctgctcgtgg tgaccgaagg ggacaacgcc accttcacct gcagcttctc caacacatcg       180
gagagcttcg tgctaaactg gtaccgcatg agccccagca accagacgga caagctggcc       240
gccttccccg aggaccgcag ccagcccggc caggactgcc gcttccgtgt cacacaactg       300
cccaacgggc gtgacttcca catgagcgtg gtcagggccc ggcgcaatga cagcggcacc       360
tacctctgtg gggccatctc cctggccccc aaggcgcaga tcaaagagag cctgcgggca       420
gagctcaggg tgacagagag aagggcagaa gtgcccacag cccacccccag ccctcaccc       480 aggccagccg gccagttcca aaccctggtg ttttgggtgc tggtggtggt tggtggagtc       540
ctggcttgct atagcttgct agtaacagtg gcctttatta ttttctgggt gaggagtaag       600
aggagcaggc tcctgcacag tgactacatg aacatgactc ccgccgccc ggcccacc         660 cgcaagcatt accagcccta tgccccacca cgcgacttcg cagcctatcg ctcctaa         717
```

<210> SEQ ID NO 12
<211> LENGTH: 720
<212> TYPE: DNA
<213> ORGANISM: Artificial Sequence
<220> FEATURE:
<223> OTHER INFORMATION: Chemically synthesized

<400> SEQUENCE: 12

```
atgcagatcc cacaggcgcc ctggccagtc gtctgggcgg tgctacaact gggctggcgg        60
ccaggatggt tcttagactc cccagacagg ccctggaacc cccccacctt ctccccagcc       120
ctgctcgtgg tgaccgaagg ggacaacgcc accttcacct gcagcttctc caacacatcg       180
gagagcttcg tgctaaactg gtaccgcatg agccccagca accagacgga caagctggcc       240
gccttccccg aggaccgcag ccagcccggc caggactgcc gcttccgtgt cacacaactg       300
cccaacgggc gtgacttcca catgagcgtg gtcagggccc ggcgcaatga cagcggcacc       360
tacctctgtg gggccatctc cctggccccc aaggcgcaga tcaaagagag cctgcgggca       420
gagctcaggg tgacagagag aagggcagaa gtgcccacag cccacccccag ccctcaccc       480 aggccagccg gccagttcca aaccctggtg atccttgtga tcttctctgg aatgttcctt       540
gttttcaccc tggccgggc cctgttcctc catcaacgaa ggaaatatag atcaaacaaa       600
ggagaaagtc ctgtggagcc tgcagagcct tgtcgttaca gctgcccag ggaggaggag        660 ggcagcacca tccccatcca ggaggattac cgaaaaccgg agcctgcctg ctcccctaa        720
```

SWITCH COSTIMULATORY RECEPTORS

CROSS-REFERENCE TO RELATED APPLICATIONS

This application is a divisional of U.S. patent application Ser. No. 14/232,557, filed Apr. 15, 2014, which is a U.S. national phase application filed under 35 U.S.C. § 371 claiming benefit to International Patent Application No. PCT/US2012/048543 filed Jul. 27, 2012, which is entitled to priority under 35 U.S.C. § 119 (e) to U.S. Provisional Patent Application No. 61/513,259, filed on Jul. 29, 2011, each of which applications are hereby incorporated by reference in their entirety.

STATEMENT REGARDING FEDERALLY SPONSORED RESEARCH OR DEVELOPMENT

This invention was made with government support under grant number CA120409 awarded by the National Institutes of Health. The government has certain rights in the invention.

BACKGROUND OF THE INVENTION

The general principle of the immune system is that T cells sense their microenvironment, and then either are activated or inhibited, depending on the signals that they sense. The CD28 gene family is comprised of 2 genes that transmit positive signals, CD28 and ICOS, and 3 genes that deliver negative signals: CTLA4, PD-1 and BTLA (Riley et al., 2005, Blood 105:13-21). The ligands for PD-1 are PDL1 and PDL2. It is well known that PD-1 ligands are often expressed in the tumor microenvironment, and that the engagement of PD-1 on T cells by PDL1 or PDL2, can lead to T cell inactivation.

At this time the only approach to prevent the negative signals delivered by PD-1 or BTLA ligands is to give antagonistic antibodies or fusion proteins that bind to PD-1 or BTLA, an approach that is now being tested in early phase trials (Cheever et al., 2008, Immunol Rev 222:357-68). Another approach would be to give small molecule compounds that might inhibit PD-1 signal transduction or BTLA signal transduction. Current approaches for preventing T cell inactivation by PD-1 is to give systemic treatment to the patient with PD-1 antagonistic antibodies.

Both of the above approaches have limitations in that T cells residing in both the tumor microenvironment as well as the entire immune system are prevented from inactivation by the systemic treatment, and this is expected to lead to autoimmunity or systemic inflammatory syndromes in some patients (Beck et al., 2006, J Clin Oncol 24:2283-9; Blansfield et al., 2005, J Immunother 28:593-8; Dougan et al., 2009, Annual Review of Immunology 27:83-117).

Thus, there is an urgent need in the art for compositions and methods for an effective form of adoptive therapy. The present invention addresses this need.

SUMMARY OF THE INVENTION

The present invention provides a fusion protein comprising a first domain and a second domain, wherein the first domain is a polypeptide that is associated with a negative signal and the second domain is a polypeptide that is associated with a positive signal.

In one embodiment, the first domain is at least a portion of the extracellular domain of the polypeptide that is associated with a negative signal and the second domain is at least a portion of the intracellular domain of the polypeptide that is associated with a positive signal.

In one embodiment, the fusion protein further comprises a transmembrane domain. In another embodiment, the transmembrane domain is the transmembrane domain of the polypeptide that is associated with a negative signal or the transmembrane domain of the polypeptide that is associated with a positive signal.

In one embodiment, the polypeptide that is associated with a negative signal is selected from the group consisting of CTLA4, PD-1 and BTLA.

In one embodiment, the polypeptide that is associated with a positive signal is selected from the group consisting of CD28 and ICOS.

The invention also provides a cell engineered to express a fusion protein comprising a first domain and a second domain, wherein the the domain is a polypeptide that is associated with a negative signal and the second domain is a polypeptide that is associated with a positive signal.

In one embodiment, the cell further comprises a chimeric antigen receptor (CAR), wherein the CAR comprises an antigen recognition domain of a specific antibody and an intracellular domain of the CD3-zeta chain.

The invention also provides a vector comprising a first domain and a second domain, wherein the first domain is a polypeptide that is associated with a negative signal and the second domain is a polypeptide that is associated with a positive signal.

The invention provides a method of treating a cancer patient. In one embodiment, the method comprises administering to the patient a T cell genetically engineered to express a fusion protein comprising a first domain and a second domain, wherein the first domain is a polypeptide that is associated with a negative signal and the second domain is a polypeptide that is associated with a positive signal.

In one embodiment, the T cell is further genetically engineered to express a CAR, wherein the CAR comprises an antigen recognition domain of a specific antibody and an intracellular domain of the CD3-zeta chain.

In one embodiment, the T cell is an autologous T cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A is an image depicting a schematic representation of chimeric switch receptors. FIG. 1B is an image demonstrating that surface expression of BTLA was detected by HVEM-Fc fusion protein at different time as indicated. FIG. 1C is an image depicting IL-2 produced by electroporated T cells that were either stimulated with BTLA ligand negative cell line (KTPloCD86A2) or BTLA ligand HVEM positive cell line (KTPloCD86A2 HVEM). Twenty-four hours post stimulation, IL-production was assayed by ELISA. The results showed that by fusing BTLA extracellular domain with intracellular domains of both ICOS and CD3 zeta, T cells could be activated by stimulation of BTLA ligand HVEM expressing cell line, indication BTLA signal could be converted to other signals in the form of a chimeric co-stimulatory receptor.

FIG. 2, comprising

FIG. 3, comprising FIGS. 3A and 3B, is a series of images demonstrating that BTLA signal can converted to ICOS signal though BTLA-ICOS CCR. The results showed that ICOS signal converted from BTLA-ICOS enhanced Th17 cell production.

FIG. 4, comprising

FIG. 6, comprising

DETAILED DESCRIPTION

Figure 1A:
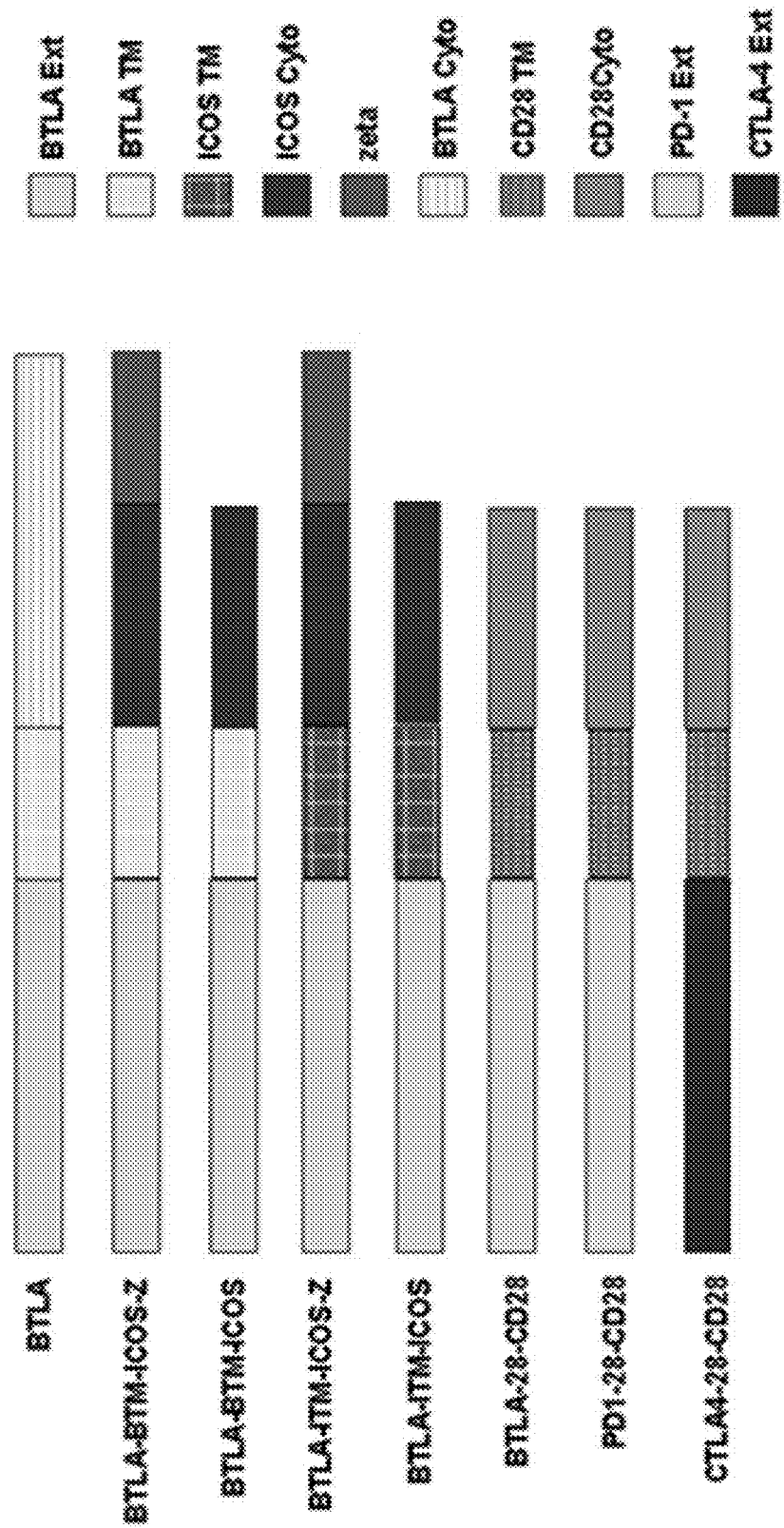
FIGS. 1A through 1C, is a series of images demonstrating that BTLA signal can be converted to other signals in the form of a chimeric co-stimulatory receptor (CCR) or otherwise referred to as a switch receptor.

The present invention relates generally to a fusion protein receptor that when displayed on a cell can convert a negative signal into a positive signal to the cell. The fusion protein is a chimeric protein in that the protein comprises at least two domains, wherein the first domain is a polypeptide that is associated with a negative signal and the second domain is a polypeptide that is associated with a positive signal. In one embodiment, the first domain binds to an inhibitory factor and activates the fusion protein wherein the signal is sent through the second domain resulting in a positive signal transmitted to the cell. In this manner, the fusion protein is able to convert an otherwise negative signal into a positive signal in the cell. Thus, the invention can be considered to encompass switch receptors that are able to switch negative signals to positive signals for enhancement of an immune response. The enhancement of an immune response can treat a disease associated with an inadequate immune response.

The invention is based on the discovery that T cells can be engineered to express a switch receptor in order to take advantage of the fact that T cells are able to sense their microenvironment to either be activated or inhibited depending on the signals that they sense. For example, the present invention takes advantage of the fact there are ligands present in the tumor microenvironment that inhibit the activity of T cells. T cells are engineered to express a switch receptor wherein the first domain is able to be activated by the inhibitory ligands in the tumor microenvironment and switch the otherwise inhibitory signal into a positive signal to the T cell byway of signaling through the second domain of the switch receptor. Thus, the invention provides a therapy that provides an improved therapeutic index with less toxicity as well as the ability to provide a one-time treatment that is effective, and avoids the need for the continuing administration of antibodies.

In some instances, the cells are genetically modified prior to administering them to a patient in need thereof. Preferably, the cell can be genetically modified to stably express a desired switch receptor of the invention. In other instances, the cells can be further modified to express an antibody binding domain on its surface, conferring novel antigen specificity that is MHC independent (e.g., chimeric antigen receptors (CAR)). CAR combines an antigen recognition domain of a specific antibody with an intracellular domain of the CD3-zeta chain or FcγRI protein into a single chimeric protein. In this context, the cell is engineered to express both a switch receptor and a CAR.

The modified cells of the invention are able to replicate in vivo resulting in long-term persistence that can lead to sustained tumor control.

The present invention further provides methods for making the present switch receptors, and methods for using these switch receptors in the study and treatment of cancer.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" can be used to refer to any material derived from the same individual to which it is later to be re-introduced into the individual.

"Allogeneic" refers to a graft derived from a different animal of the same species.

"Xenogeneic" refers to a graft derived from an animal of a different species.

As used herein, "biologically active or immunologically active" refers to fusion proteins according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild type proteins which are the building blocks of the fusion proteins of the present invention.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

By "chimeric protein" is meant any single polypeptide unit that comprises two distinct polypeptide domains, wherein the two domains are not naturally occurring within the same polypeptide unit. Typically, such chimeric proteins are made by expression of a cDNA construct but could be made by protein synthesis methods known in the art.

The term "derivative" as used herein in relation to the amino acid sequence means chemical modification of a fusion protein of the invention.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fusion proteins" refers to chimeric proteins comprising amino acid sequences of two or more different proteins. Typically, fusion proteins result from in vitro recombinatory techniques well known in the art.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells. Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, and the like.

"Immune cell," as the term is used herein, means any cell involved in the mounting of an immune response. Such cells include, but are not limited to, T cells, B cells, NK cells, antigen-presenting cells, and the like.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating" an immune response, as used herein, is meant mediating a detectable increase or decrease in the level of an immune response in a mammal compared with the level of an immune response in the mammal in the absence of a treatment or compound, and/or compared with the level of an immune response in an otherwise identical but untreated mammal. The term encompasses perturbing and/or affecting a native signal or response thereby mediating a beneficial therapeutic response in a mammal, preferably, a human.

"Negative signal", as used herein, means a signal that induces the typical cascade of intracellular events associated with among other things, decrease proliferation, decrease activation, decrease cellular processing, and the like.

"Positive signal", as used herein, means a signal that induces the typical cascade of intracellular events associated with among other things increase, proliferation, increase activation, increase cellular processing, and the like.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division. Activation can also be associated with generating an immune response (e.g., a mitogen such as ConA or PHA), detectably upregulates surface markers, such as CD25, i.e., the IL2 receptor, initiates a phosphorylation cascade involving p56lck, causes the release of cytokines and interleukins, increases DNA synthesis which can be assessed by, among other methods, assessing the level of incorporation of $^3$H-thymidine into nascent DNA strands, and causes the cells to proliferate.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the discovery that a chimeric switch receptor can be designed to switch a negative signal transduction signal into a positive signal. In one embodiment, the switch receptor is a chimeric protein comprising a first protein or fragment thereof associated with a negative signal and a second protein or fragment thereof associated with a positive signal. An example of a protein associated with a negative signal includes but is not limited to CTLA-4, PD-1, BTLA, and the like. An example of a protein associated with a positive signal includes but is not limited to CD28, ICOS, and the like.

The invention relates to chimeric switch receptors and related fusion proteins, and methods of treating cancer with these proteins.

In one embodiment, the invention provides a cell (e.g., T cell or natural killer cell) engineered to express a chimeric switch receptor wherein the engineered cell exhibits an antitumor property. In some instances, the engineered cell is also engineered to express a chimeric antigen receptor (CAR). In some instances, the engineered cell of the invention exhibits enhanced IL-2 and IFN-γ production. In some instances, the engineered cell of the invention is polarized to secrete IL-17. Therefore, the engineered cell of the invention when infused into a patient can eliminate tumor cells in vivo in the patient.

Compositions

The present invention provides, in one aspect, a switch receptor which when expressed in a cell converts a negative signal into a positive signal in the cell. For example, this switch receptor has a first domain that comprises a polypeptide that delivers a negative signal; and a second domain that comprises a polypeptide that delivers a positive signal.

In one embodiment, a polypeptide that has the capacity to deliver a negative signal includes but is not limited to CTLA4, PD-1, BTLA, and the like.

In one embodiment, a polypeptide that has the capacity to deliver a positive signal includes but is not limited to ICOS, CD28, and the like. Suitable first domains in the context of a polypeptide that delivers a negative signal include, variants or derivatives of wild-type CTLA4. Preferably, the first domain of the switch receptor of this embodiment is at least a portion of the extracellular domain of the CTLA protein, specifically that portion of the extracellular domain which is necessary for binding to the natural ligand of CTLA. Variants of the wild-type form of the extracellular domain, or the portion of the extracellular domain responsible for binding to the natural ligand of CTLA, are also included in the present invention, so long as the variant provides a similar level of biological activity as the wild-type protein.

Suitable first domains in the context of a polypeptide that delivers a negative signal include, variants or derivatives of wild-type PD-1. Preferably, the first domain of the switch receptor of this embodiment is at least a portion of the extracellular domain of the PD-1 protein, specifically that portion of the extracellular domain which is necessary for binding to the natural ligand of PD-1. Variants of the wild-type form of the extracellular domain, or the portion of the extracellular domain responsible for binding to the natural ligand of PD-1, are also included in the present invention, so long as the variant provides a similar level of biological activity as the wild-type protein.

Suitable first domains in the context of a polypeptide that delivers a negative signal include, variants or derivatives of wild-type BTLA. Preferably, the first domain of the switch receptor of this embodiment is at least a portion of the extracellular domain of the BTLA protein, specifically that portion of the extracellular domain which is necessary for binding to the natural ligand of BTLA. Variants of the wild-type form of the extracellular domain, or the portion of the extracellular domain responsible for binding to the natural ligand of BTLA, are also included in the present invention, so long as the variant provides a similar level of biological activity as the wild-type protein.

Suitable second domains in the context of a polypeptide that delivers a positive signal include, variants or derivatives of the ICOS protein. Preferably, the second domain of the switch receptor in this embodiment is at least a portion of the intracellular domain (also referred to as endodomain) of the ICOS protein, specifically that portion which is necessary for triggering a signal to intracellular components of the cell. Variants of the wild-type form of the intracellular domain of the ICOS protein, or the portion of the intracellular domain responsible for signaling, are also included in the present invention, so long as the variant provides a similar level of biological activity as the wild-type protein.

Suitable second domains in the context of a polypeptide that delivers a positive signal include, variants or derivatives of the CD28 protein. Preferably, the second domain of the switch receptor in this embodiment is at least a portion of the intracellular domain (also referred to as endodomain or cytoplasmic) of the CD28 protein, specifically that portion which is necessary for triggering a signal to intracellular components of the cell. Variants of the wild-type form of the intracellular domain of the CD28 protein, or the portion of the intracellular domain responsible for signaling, are also included in the present invention, so long as the variant provides a similar level of biological activity as the wild-type protein.

The switch receptor of the invention comprises a polypeptide corresponding to a cytoplasmic, transmembrane and extracellular domain, as well as polypeptides corresponding to smaller portions of the cytoplasmic, transmembrane and extracellular domain. In one embodiment the switch receptor comprises the transmembrane domain of the first polypeptide that delivers a negative signal. In another embodiment, the switch receptor comprises the transmembrane domain of the second polypeptide that delivers a positive signal.

In yet an additional aspect of the present invention, the first polypeptide that delivers a negative signal component of any of the switch receptors described herein can be substituted with another inhibitory protein, i.e. a protein which prevents activation of an immune response and/or induces apoptosis in T cells or other cell types, such as B cells, natural killer (NK) cells, NKT cells, lymphoid progenitor cells, dendritic cells, monocytes/macrophages, tissue-based macrophage lineage cells with antigen-presenting capacity, and any one of a number of non-professional antigen-presenting cells, for example, endothelial cells. Examples of inhibitory proteins include, but are not limited to ligands to PD-1, CTLA-4, BTLA, CD160, CD161 and CD94; LAG-3, and CD244 (see 2011, Wherry, Nat Immunol. 131:492-9).

Any suitable first polypeptide that delivers a negative signal can be used according to the present invention, provided the polypeptide binds to the corresponding ligand, and through this binding event leads to a activation of the switch receptor. According to one embodiment of the present invention, the engagement of the first polypeptide that delivers a negative signal of the switch receptor with its corresponding ligand results in the activation of the second polypeptide that delivers a positive signal of the switch receptor. In this manner, a negative signal can be converted to a positive signal. That is, the first polypeptide of the switch receptor of the present invention can trigger an intracellular signaling pathway whereby the activation of the second polypeptide of the invention results in the conversion of the negative signal into a positive signal. Thus, a unique feature of the first polypeptide of the switch receptor of the present invention is that it converts a natural trans signal that naturally would result in a negative signal to the cell into a positive signal that induces the cell to exhibit antitumor characteristics.

Similarly, any suitable second polypeptide can be used, provided the protein can send a positive signal to a cell, that is distinct from the trans signal associated with the first polypeptide component of the switch receptor. The second polypeptide can be a protein that sends a positive signal or an activating signal. A preferred example of the second polypeptide of the invention includes but is not limited to CD28, CD27, ICOS, CD137 (4-1BB), and TCRzeta.

In one embodiment, the invention takes advantage of microenvironments where there is a large number of ligands or proteins that inhibit the immune system wherein inhibition of the immune system results in an undesirable disease state. That is, the switch receptor can be engineered to comprise a first domain that binds to the immune inhibitory factor in the microenvironment and converts the signal normally associated with the immune inhibitory factor into a positive signal where the positive signal activates the cell to exhibit an enhanced immune response.

A preferred chimeric protein of the present invention is BTLA:ICOS. Genetic chimerization of BTLA with ICOS sequences and recombinant expression results in chimeric BTLA:ICOS "switch receptor" that demonstrate structural and functional characteristics attributable to both BTLA and ICOS. Cells engineered to express BTLA: ICOS can redirect inhibitory signaling to stimulatory signal and thereby enhance T cell function. In some instances, cells are engineered to express the BTLA: ICOS switch receptor in combination with CAR.

Another preferred chimeric protein of the present invention is PD1:CD28. Genetic chimerization of PD1 with CD28 sequences and recombinant expression results in chimeric PD1:CD28 "switch receptor" that demonstrate structural and functional characteristics attributable to both PD1 and CD28. Cells engineered to express PD1:CD28 can redirect inhibitory signaling to stimulatory signal and thereby enhance T cell function. In some instances, cells are engineered to express the PD1:CD28 switch receptor in combination with CAR.

Another preferred chimeric protein of the present invention is CTLA4:CD28. Genetic chimerization of CTLA4 with CD28 sequences and recombinant expression results in chimeric CTLA4:CD28 "switch receptor" that demonstrate structural and functional characteristics attributable to both CTLA4 and CD28. Cells engineered to express CTLA4:CD28 can redirect inhibitory signaling to stimulatory signal and thereby enhance T cell function. In some instances, cells are engineered to express the CTLA4:CD28 switch receptor in combination with CAR.

The present proteins can exist in numerous forms. For example, the present proteins can be in the form of a linear or branched polypeptide. Linear chimeric proteins can be produced by recombinant DNA technology. For example, chimeric transcription cassettes can be assembled using restriction endonuclease site overlap or the polymerase chain reaction (PCR)-based splice-by-overlap-extension.

Branched polypeptide chimeric proteins can be readily produced by template-assembled synthetic peptide (TASP) technology (Mutter, Trends Biochem. Sci. 13:260-265 (1988)). By this process, the peptide units are synthesized separately and covalently coupled to a multifunctional carrier, such as a core peptide, using chemical coupling reagents. For example, a cyclic decapeptide analogue of gramicidin S, in which two antiparallel beta-sheet segments (lys-ala-lys) are linked by two beta-turns, can be used as a core peptide. Segment condensation strategies can be used to attach the first and second proteins to the epsilon-amino groups of the 4 lysine side chains.

The present proteins can also exist as two or more separate proteins linked together by a bridge, such as a chemical link. For example, two or more protein components can be covalently linked directly to each other in branched structures using chemical cross-linking reagents such as dithio-bis(succinimidyl proprionate) (DSP). By this methodology, for example, the first and second proteins can be directly linked.

The particular first and second polypeptides of the chimeric switch receptor of the invention can vary depending on the illness being treated. Typically, for example, when treating cancer or viral infections, second polypeptides that stimulate immune cell responses are used. When treating immune system disorders where pathogenic immune responses exist, an inhibitory second polypeptide is used. Thus, for cancer and viral diseases, switch receptors that convert inhibitory to activating immune activation signals are desired. In contrast, for autoimmune diseases, chimeric switch receptors that convert activating to inhibitory immune signals are desired. In this setting, the immune-inhibitory second protein component can be directed to different pathogenic immune effectors, including T cells, B cells, natural killer cells, and antigen-presenting cells.

Accordingly, the invention provides a switch receptor which when expressed in a cell converts a positive signal into a negative signal in the cell. For example, this switch receptor contains a first domain that comprises a polypeptide that delivers a positive signal; and a second domain that comprises a polypeptide that delivers a negative signal in the cell.

Genetic Modification

The present invention encompasses a cell (e.g., T cell) transduced with a lentiviral vector (LV). In one embodiment, the LV encodes the switch receptor of the invention comprising a first domain that comprises a polypeptide that delivers a negative signal and a second domain that comprises a polypeptide that delivers a positive signal.

In one embodiment, the cell can be further be transduced with a LV encoding a chimeric antigen receptor (CAR) which combines an antigen recognition domain of a specific antibody with an intracellular domain of the CD3-zeta chain or FcγRI protein into a single chimeric protein.

Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids of the invention is typically achieved by operably linking a nucleic acid encoding the desired polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, N Y 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Therapeutic Application

The present invention includes a type of cellular therapy where T cells are genetically modified to express a switch receptor and the engineered T cell is infused to a recipient in need thereof. The infused cell is able to kill tumor cells in the recipient. Unlike antibody therapies, engineered T cells of the invention are able to replicate in vivo resulting in long-term persistence that can lead to sustained tumor control.

The present invention is also directed to methods for treating a patient for an illness comprising administering to the patient an effective amount of the engineered switch receptors of the present invention. Various illnesses can be treated according to the present methods, including but not limited to cancer, such as ovarian carcinoma, breast carcinoma, colon carcinoma, glioblastoma multiforme, prostate carcinoma and leukemia; viral infections, such as chronic viral infections with HBV, HCV, HTLV-1, HTLV-II, EBV, HSV-I, HSV-II, and KSHV; and autoimmune diseases, such as arthritis, asthma, graft-versus-host disease, organ rejection, psoriasis, systemic lupus erythematosis, atopic allergy, inflammatory bowel disease, multiple sclerosis, allergic dermatitis, Sjogren's syndrome, progressive systemic sclerosis, autoimmune thyroiditis, autoimmune diabetes, autoimmune liver diseases, and bone marrow myelodysplastic syndromes.

Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulvar cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia, chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal.

Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success.

In the context of treatment for cancer, the switch receptors of the present invention can optionally be administered to a patient in combination with other chemotherapeutic agents. Suitable chemotherapeutic agents include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above.

Also included are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Also included are chemotherapeutic agents that are able to sensitize tumor cells to TRAIL and overcome TRAIL resistance, such as proteasome inhibitors and histone deacetylase (HDAC) inhibitors, cycloheximide, imatinib mesylate and other protein tyrosine kinase inhibitors, 17-allylamino-17-demethoxygeldanamycin, arsenic trioxide and X-linked Inhibitors of Apoptosis Protein small molecule antagonists; and pharmaceutically acceptable salts, acids or derivatives of any of these.

Additional information on the methods of cancer treatment is provided in U.S. Pat. No. 7,285,522, incorporated by reference in its entirety.

Accordingly, in a preferred embodiment, the switch receptors of the present invention can be used to treat breast cancer. In another preferred embodiment, the switch receptors of the invention can be used to treat colon cancer. In another embodiment, the switch receptors of the invention can be used to treat liver cancer. In another preferred embodiment, the switch receptors of the invention can be used to treat ovarian cancer. In another embodiment, the switch receptors of the invention can be used to treat leukemia. In another embodiment, the switch receptors of the invention can be used to treat melanoma. In further embodiments, the switch receptors of the present invention can be used to treat alloimmune diseases, for example graft rejection, or graft-versus-host or host-versus-graft disease.

Typically, for each disease application, a small "library" of candidate switch receptors can be generated and comparatively evaluated in appropriate and well-established ex vivo and in vivo models to determine relative efficacies and toxicities.

The particular first and second proteins used in the methods will vary depending on the illness being treated. Generally, for cancer, switch receptors that convert inhibitory to activating immune trans activation signals are desired. Without wishing to be bound by any particular theory, the anti-tumor immunity response elicited by the engineered cell of the invention may be an active or a passive immune response. The response may be part of an adoptive immunotherapy approach.

With respect to ex vivo immunization, at least one of the following occurs in vitro prior to administering the cell into a mammal: i) expansion of the cells, ii) introducing a nucleic acid encoding a switch receptor of the invention to the cells or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a switch receptor of the invention. The engineered cell can be administered to a mammalian recipient to provide a therapeutic benefit. The mammalian recipient may be a human and the engineered cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the engineered cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the engineered T cells of the invention.

The engineered T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, irrimunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993; Isoniemi (supra)). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Switch Receptors

The results presented herein demonstrate that chimeric receptors can be engineered to convert negative signals into positive signals on T cells. Experiments were designed to develop a method that avoids inhibition of a tumor inhibitory factor systemically and therefore the entire immune system. Briefly, T cells were engineered to express a chimeric receptor that encoded the PD-1 extracellular domain (without the inhibitory PD-1 domain) and a stimulatory CD28 or ICOS signaling domain. The orientation of the chimeric receptor placed the PD-1 extracellular domain outside the cell and the CD28 or ICOS stimulatory domain inside the T cell. Thus the interaction of T cells with tumor antigens in the tumor microenvironment is positively influenced upon the engagement of PD-1 ligands because the signal in the cell is delivered by the CD28 or ICOS signaling endodomain rather than the native inhibitory PD-1 endodomain.

The materials and methods employed in these experiments are now described.

Materials and Methods

Switch Receptor Production

Constructs were designed for the testing of BTLA switch receptor. The following are sequence of each construct that were cloned into pGEM.64A based IVT vector.

BTLA;
SEQ ID NO: 1
Atgaagacattgcctgccatgcttggaactgggaaattattttgggtctt cttcttaatcccatatctggacatctggaacatccatgggaaagaatcat gtgatgtacagctttatataaagagacaatctgaacactccatcttagca ggagatccattgaactagaatgccctgtgaaatactgtgctaacaggcct catgtgacttggtgcaagctcaatggaacaacatgtgtaaaacttgaaga tagacaaacaagttggaaggaagagaagaacatttcatttttcattctac attttgaaccagtgcttcctaatgacaatgggtcataccgctgttctgca aattttcagtctaatctcattgaaagccactcaacaactctttatgtgac agatgtaaaaagtgcctcagaacgaccctccaaggacgaaatggcaagca gaccctggctcctgtatagtttacttcctagggggattgcctctactca tcactacctgtactgcctgttctgctgcctgagaaggcaccaaggaaagc aaaatgaactctctgacacagcaggaagggaaattaacctggttgatgct caccttaagagtgagcaaacagaagcaagcaccaggcaaaattcccaagt actgctatcagaaactggaatttatgataatgaccctgacctttgtttca ggatgcaggaagggtctgaagtttattctaatccatgcctggaagaaaac aaaccaggcattgtttatgcttccctgaaccattctgtcattggaccgaa ctcaagactggcaagaaatgtaaaagaagcaccaacagaatatgcatcca tatgtgtgaggagttaa BTLA-BTM-CD28;
SEQ ID NO: 2
Aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg taaaacttgaagatagacaaacaagttggaaggaagagaagaacatttca ttttcattctacattttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagt*ttacttcctttgggggg*

*attgcctctactcatcactacctgtttctgcctgttctgctgcctg*gagg agtaagaggagcaggctcctgcacagtgactacatgaacatgactcccg ccgccccgggcccacccgcaagcattaccagccctatgccccaccacgcg acttcgcagcctatcgctcctgataagcggccgca BTLA-BTM-CD27;
SEQ ID NO: 3
Aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg taaaacttgaagatagacaaacaagttggaaggaagagaagaacatttca ttttcattctacattttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagt*ttacttcctttgggggg*

*attgcctctactcatcactacctgtttctgcctgttctgctgcctg*gaag gaaatatagatcaaacaaggagaaagtcctgtggagcctgcagagcctt gtcgttacagctgccccaggaggaggagggcagcaccatcccatccag gaggattaccgaaaaccggagcctgcctgctcccctgataagcggccgc a BTLA-ITM-CD28;
SEQ ID NO: 4
aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg -continued taaaacttgaagatagacaaacaagttggaaggaagagaagaacatttca tttttcattctacatttttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagtttctggttacccatagg atgtgcagcctttgttgtagtctgcattttgggatgcatacttattgagg agtaagaggagcaggctcctgcacagtgactacatgaacatgactccccg ccgcccgggcccaccgcaagcattaccagccctatgccccaccacgcg acttcgcagcctatcgctcctgataagcggccgca

BTLA-ITM-CD27;

SEQ ID NO: 5

Aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg taaaacttgaagatagacaaacaagttggaaggaagagaagaacatttca tttttcattctacatttttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagtttctggttacccatagg atgtgcagcctttgttgtagtctgcattttgggatgcatacttattgaag gaaatatagatcaaacaaggagaaagtcctgtggagcctgcagagcctt gtcgttacagctgccccagggaggagagggcagcaccatcccccatccag gaggattaccgaaaaccggagcctgcctgctcccctgataagcggccgc a

BTLA-BTM-ICOS;

SEQ ID NO: 6

Aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg taaaacttgaagatagacaaacaagttggaaggaagagaagaacatttca tttttcattctacatttttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagtttacttcctttggggg attgcctctactcatcactacctgtttctgcctgttctgctgcctgtgtt ggcttacaaaaaagaagtattcatccagtgtgcacgaccctaacggtgaa tacatgttcatgagagcagtgaacacagccaaaaaatctagactcacaga tgtgaccctataagcggccgca

BTLA-BTM-ICOS-Z;

SEQ ID NO: 7

Aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg taaaacttgaagatagacaaacaagttggaaggaagagaagaacatttca tttttcattctacatttttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagtttacttcctttggggg attgcctctactcatcactacctgtttctgcctgttctgctgcctgtgtt ggcttacaaaaaagaagtattcatccagtgtgcacgaccctaacggtgaa tacatgttcatgagagcagtgaacacagccaaaaaatctagactcacaga tgtgaccctatgcagagtgaagttcagcaggagcgcagacgcccccgcgt accagcagggccagaaccagctctataacgagctcaatctaggacgaaga gaggagtacgatgttttggacaagagacgtggccgggaccctgagatggg gggaaagccgagaaggaagaaccctcaggaaggcctgtacaatgaactgc agaaagataagatggcggaggcctacagtgagattgggatgaaaggcgag cgccggaggggcaaggggcacgatggcctttaccagggtctcagtacagc caccaaggacacctacgacgcccttcacatgcaggccctgccccctcgct aagcggccgca

BTLA-ITM-ICOS;

SEQ ID NO: 8

Aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac tccatcttagcaggagatccctttgaactagaatgccctgtgaaatactg tgctaacaggcctcatgtgacttggtgcaagctcaatggaacaacatgtg taaaacttgaagatagacaaacaagttggaaggaagagaagaacatttca tttttcattctacatttttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagtttctggttacccatagg atgtgcagcctttgttgtagtctgcattttgggatgcatacttatttgtt ggcttacaaaaaagaagtattcatccagtgtgcacgaccctaacggtgaa tacatgttcatgagagcagtgaacacagccaaaaaatctagactcacaga tgtgaccctataagcggccgca

BTLA-ITM-ICOS-Z,

SEQ ID NO: 9 aagcttgccgccatgaagacattgcctgccatgcttggaactgggaaatt attttgggtcttcttcttaatcccatatctggacatctggaacatccatg ggaaagaatcatgtgatgtacagctttatataaagagacaatctgaacac -continued

```
tccatcttagcaggagatcccttttgaactagaatgccctgtgaaatactg tgctaacaggcctcatgtgacttggtgcaagctcaatggaacaacatgtg taaaacttgaagatagacaaacaagttggaaggaagagaagaacatttca tttttcattctacattttgaaccagtgcttcctaatgacaatgggtcata ccgctgttctgcaaattttcagtctaatctcattgaaagccactcaacaa ctctttatgtgacagatgtaaaaagtgcctcagaacgaccctccaaggac gaaatggcaagcagaccctggctcctgtatagtttacttcctttgggggg attgcctctactcatcactacctgtttctgcctgttctgctgcctgtgtt ggcttacaaaaagaagtattcatccagtgtgcacgaccctaacggtgaa tacatgttcatgagagcagtgaacacagccaaaaaatctagactcacaga tgtgaccctatgcagagtgaagttcagcaggagcgcagacgcccccgcgt accagcagggccagaaccagctctataacgagctcaatctaggacgaaga gaggagtacgatgttttggacaagagacgtggccgggaccctgagatggg gggaaagccgagaaggaagaaccctcaggaaggcctgtacaatgaactgc agaaagataagatggcggaggcctacagtgagattgggatgaaaggcgag cgccggaggggcaaggggcacgatggcctttaccagggtctcagtacagc caccaaggacacctacgacgcccttcacatgcaggccctgcccctcgct aagcggccgca
```

Transduction of T Cells

Methods of T cell preparation using paramagnetic polystyrene beads coated with anti-CD3 and anti-CD28 monoclonal antibodies have been described (Laport et al., 2003, Blood 102:20042013). Lentiviral transduction was performed as described (Levine et al., 2006, Proc Natl Acad Sci USA 103:17372-17377). Electroporation of T cells with RNA has been described (2010, Zhao et al., Cancer Res 70:9062) as a method to express these receptors. The use of adenoviral vectors has been described (2004, Schroers et al., Exp Hematol 32:536). A number of other approaches to express proteins in T cells have been described (2009, June et al., Nat Rev Immunol 9:704).

Cytokine Analyses

Quantification of soluble cytokine factors was performed using Luminex bead array technology and kits purchased from Life technologies (Invitrogen). Assays were performed as per the manufacturer protocol with an 8 point standard curve generated using a 3-fold dilution series.

The results of the experiments are now described.

The results presented herein demonstrate that a chimeric receptor can be engineered and expressed on a T cell where the chimeric receptor converts negative signals into positive signals on the T cell. Accordingly, the invention provides a type of adoptive T cell or NK cell therapy using cells that have been genetically modified to express T cell receptors (TCRs) or chimeric antigen receptors (CARs).

Experiments were designed to develop a targeted method to avoid the inhibition of PD-1 systemically and therefore the entire immune system. The targeted method comprises administering T cells that express chimeric receptors that encode for example the PD-1 extracellular domain, and rather than the inhibitory PD-1 domain, a stimulatory CD28 or ICOS signaling domain on the intracellular part of the T cell. Thus the interaction of T cells with tumor antigens in the tumor microenvironment would be positively influenced upon the engagement of PD-1 ligands, because the signal in the cell is delivered by the CD28 or ICOS signaling endodomain, rather than the native PD-1 endodomain.

Converting BTLA Signals

In a similar approach, chimeric receptors encoding BTLA have been constructed. BTLA, along with PD-1 is also a member of the CD28 family. BTLA has several ligands, including HVEM, which is expressed on tumor cells and other cells, often within the tumor microenvironment. It is well known that BTLA interaction with natural ligands on cells negatively regulates the T-cell immune responses (Paulos et al., 2010, J Clin Invest 120:76-80; Derré et al., 2010, J Clin Invest 120:157-67; Chemnitz et al., 2006, J Immunol 176:6603-14). To circumvent chimeric receptors comprised of the BTLA extracellular domain and intercellular signaling endodomains that include CD28 or ICOS domains were constructed.

Figure 1B:
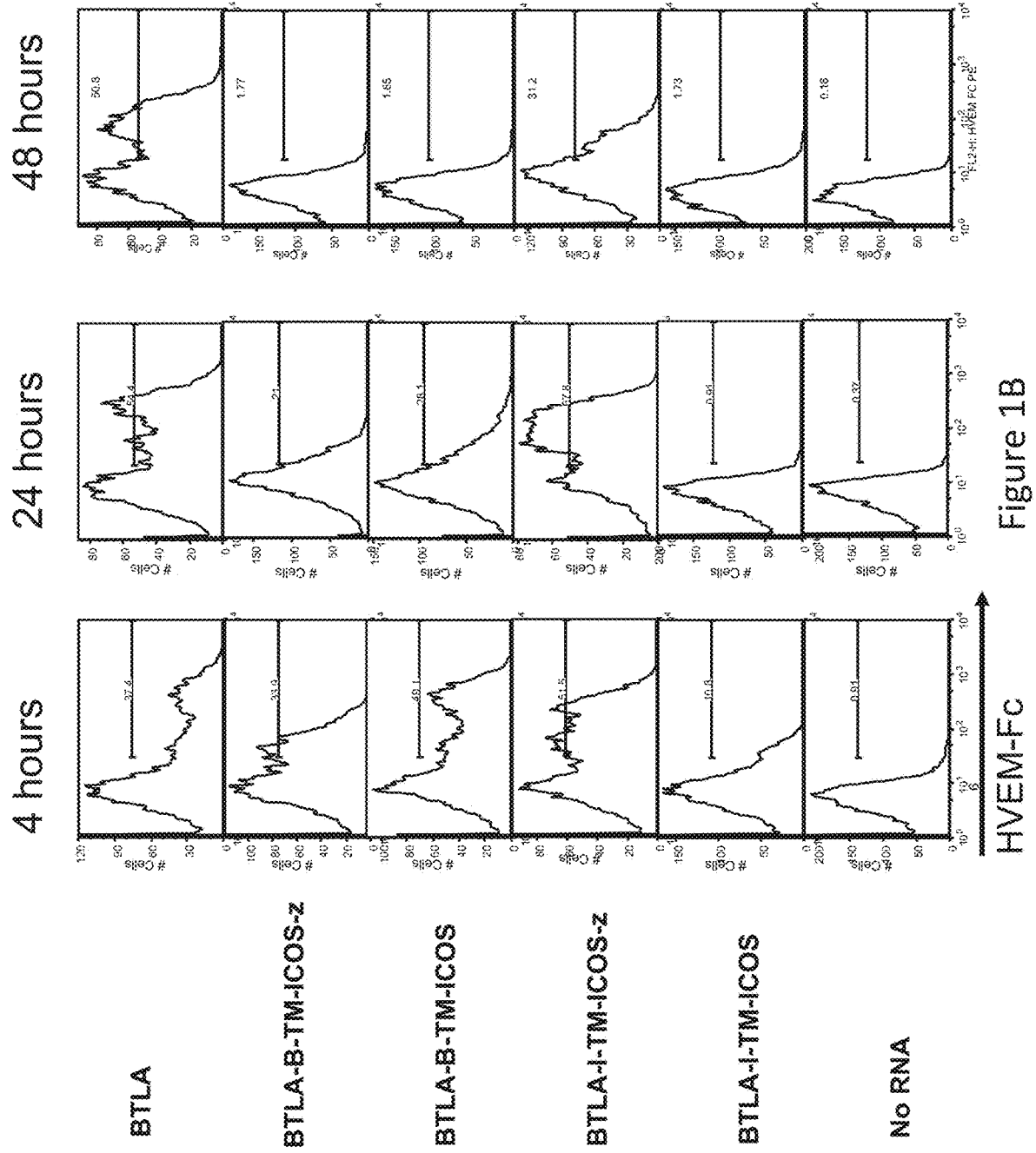
Figure 1C:
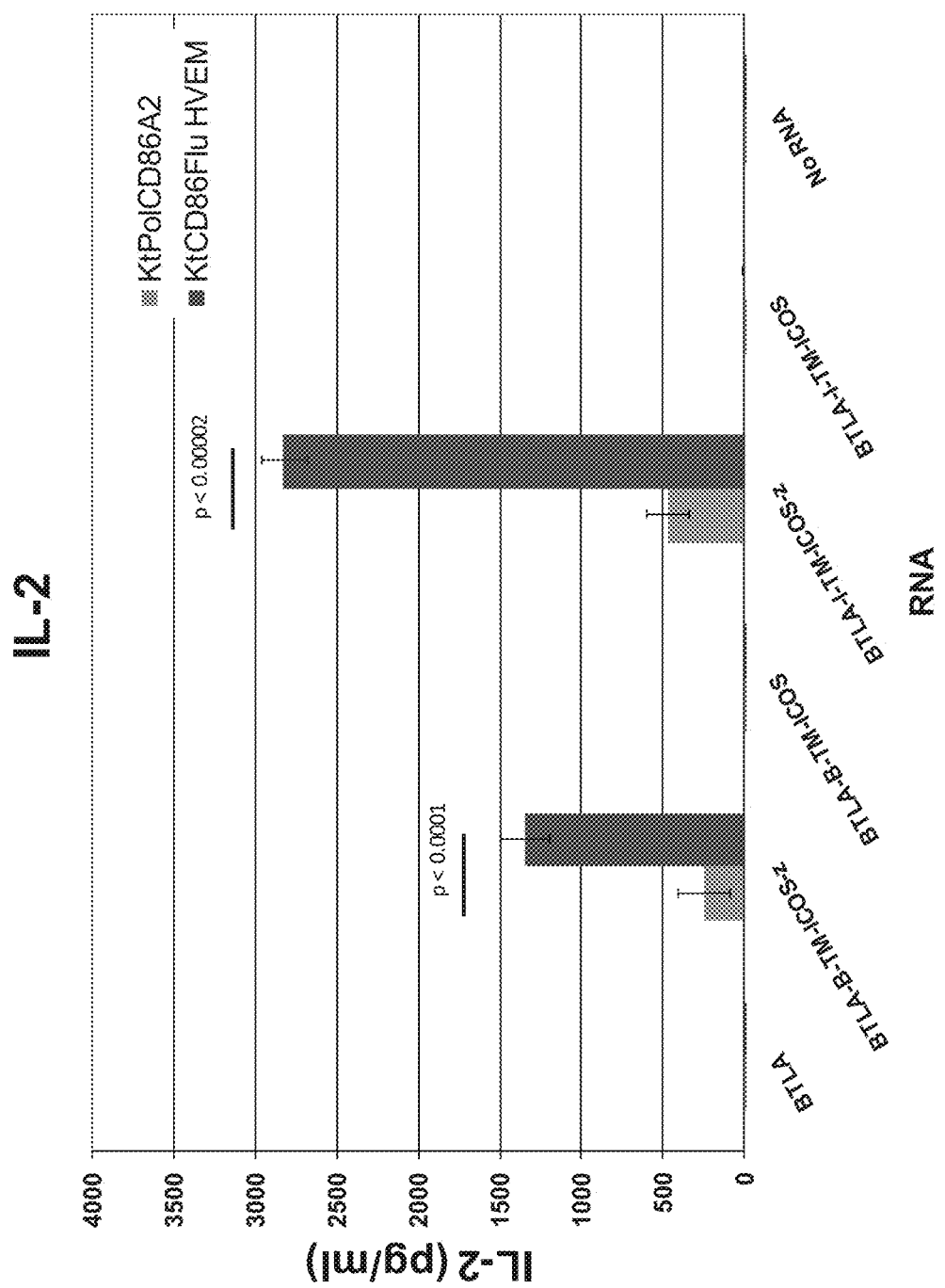

Briefly, molecular cloning was used to construct the exemplary chimeric receptors depicted in FIG. 1. To test whether ligation of BTLA CCR expressed on the T cells surface could be expressed properly and transduce signals through ICOS intracellular domain to CD3 zeta, IVT mRNAs encoding BTLA CCR as indicated were electroporated into stimulated T cells and surface expression of BTLA was detected by HVEM-Fc fusion protein at different time as indicated (FIG. 1B). Electroporated T cells were either stimulated with BTLA ligand negative cell line (KTPolCD86A2) or BTLA ligand HVEM positive cell line (KTCD86Flu HVEM). Twenty-four hours post stimulation, IL-2 produced by the T cells was assayed by ELISA (FIG. 1C). The results showed that by fusing BTLA extracellular domain with intracellular domains of both ICOS and CD3 zeta, T cells could be activated by stimulation of BTLA ligand HVEM expressing cell line, indication BTLA signal could converted to other signals in the form of chimeric co-stimulatory receptor (CCR).

Figure 2A:
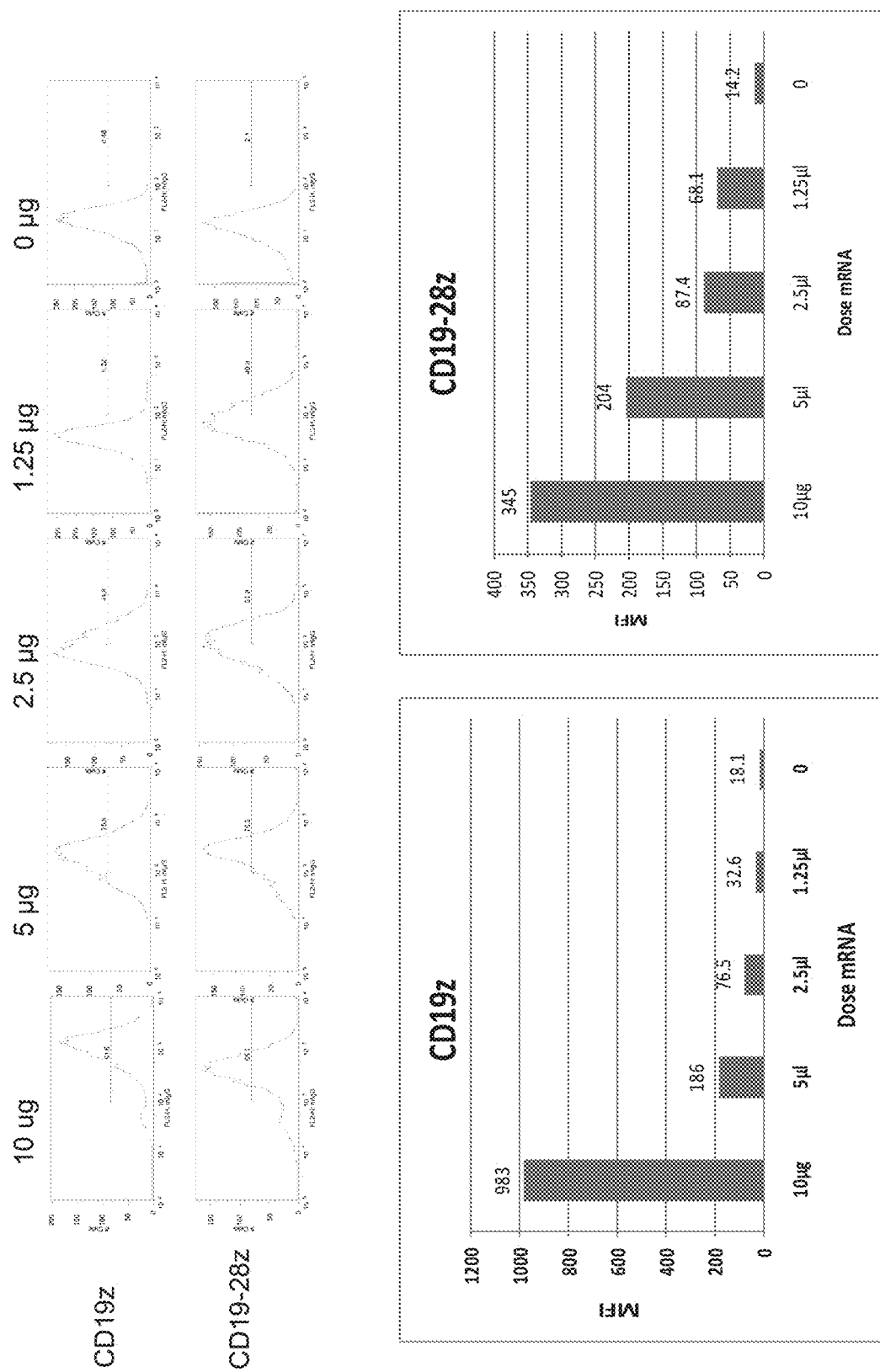
FIGS. 2A through 2C, is a series of imaged demonstrating that BTLA signal can be converted to CD28 signal though BTLA-CD28 CCR.
Figure 2B:
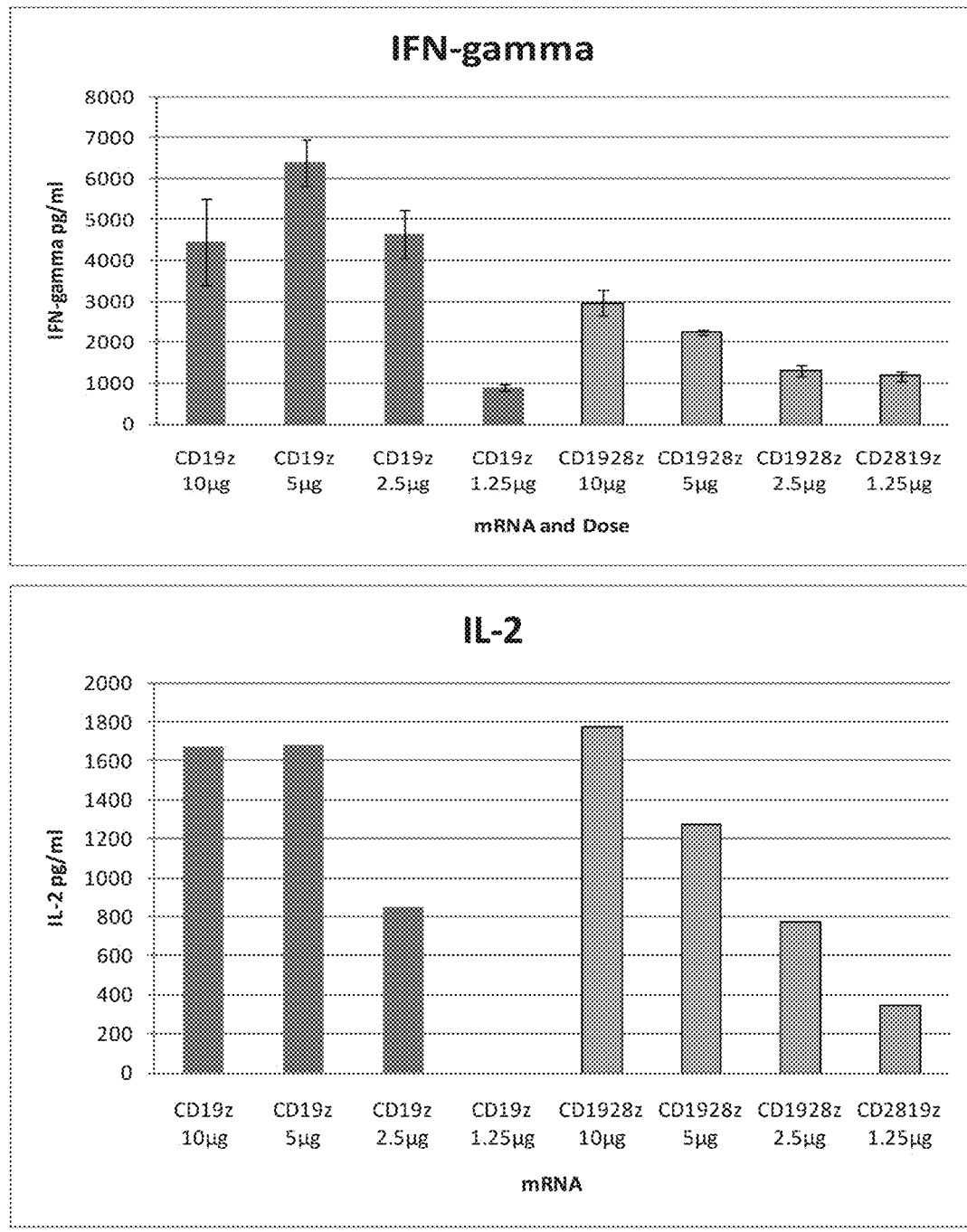

The next set of experiments was designed to assess whether the BTLA inhibitory signal could be converted to a CD28 costimulatory signal though BTLA-CD28 CCR. To find the proper window that could show CD28 signaling, different doses of RNA (ug/0.1 ml T cells) were electroporated into T cells and CAR (CD19z, CD19-28Z) expression was detected by FACS. Upper panel shows histograms and the percentage of transgene expression and the lower panel shows the MFI of transgene expression (FIG. 2A). IL2 production of RNA electroporated T cells as described in FIG. 2A were stimulated by CD19 positive cell line K562-CD19 and IL-2 production was assay by ELISA as shown in FIG. 2B. Upper panel shows IFN-gamma and lower panel shows IL-2 production. The results shows that at RNA dose of 1.5 ug, unlike CD19-28z RNA electroporated T cells, which showed over 300 pg/ml IL-2 production, there was no detectable IL-2 production for CD19z RNA electroporated T cells IFN-gamma production could be detected at similar levels for both CD19z and CD19-28Z electroporated T cells with the RNA dose of 1.5 ug. Therefore, 1.5 ug RNA was used as RNA dose to test the BTLA-CD28 signal converting polypeptide.

Figure 2C:
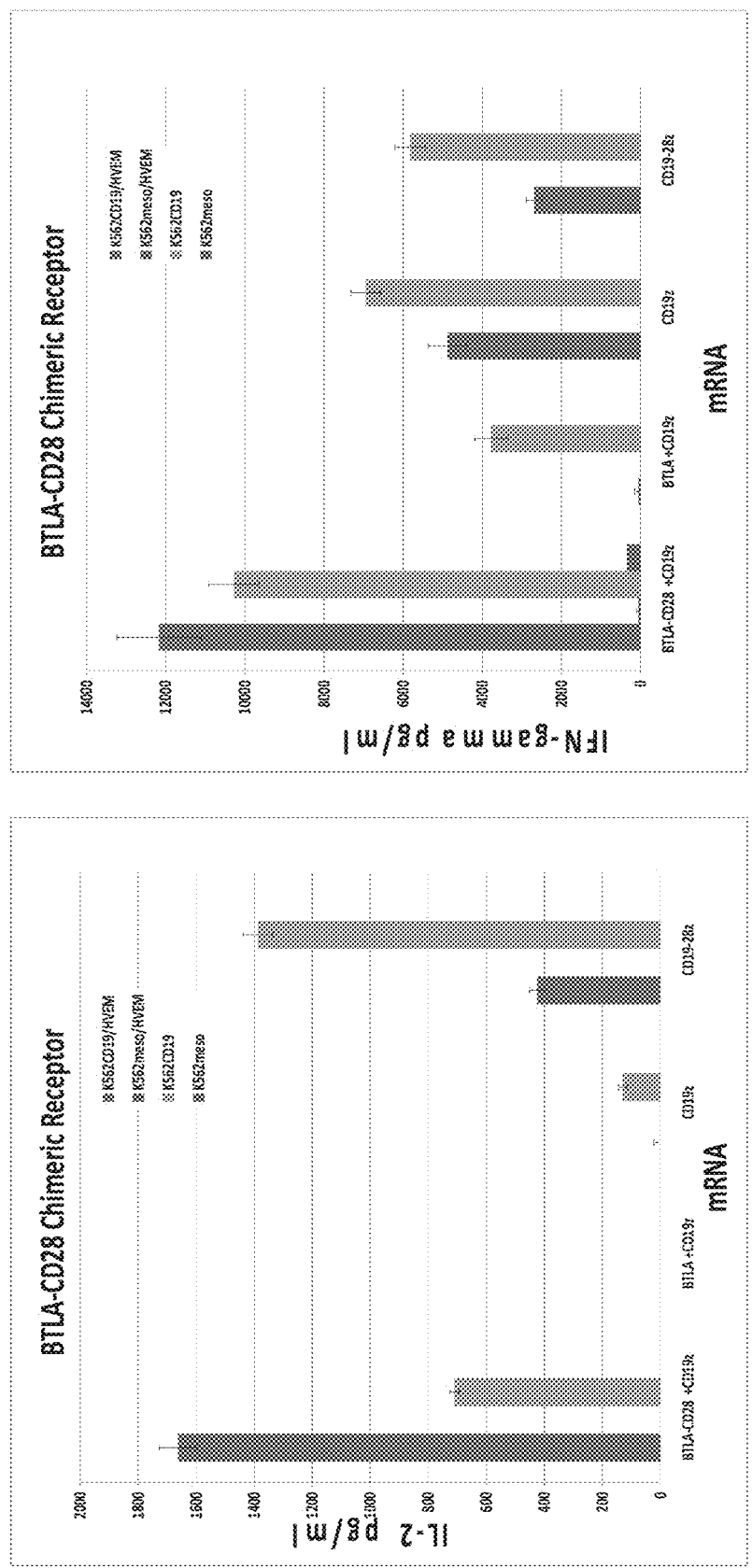

T cells were co-electroporated with 1.5 ug CD19z and BTLA CCR as indicated and stimulated with K562 expressing CD19 (K562CD19) or both CD19 and HVEM (K562CD19/HVEM). K562 lines expressing mesothelin (with or without HVEM) were used as controls (FIG. 2C. The results show that full length (wild type) BTLA suppressed both IL2 and IFN-gamma production. There was no detectable IL-2 production for T cells electroporated with only CD19z when stimulated with CD19/HVEM double positive cell line, while T cells electroporated with CD19-28z and stimulated with CD19/HVEM double positive cell line produced over 400 pg/ml IL-2. However, when T cells were co-electroporated with both CD19z and BTLA-CD28 CCR RNAs, the IL-2 production was 4 time higher than CD19-28z electroporated T cells, when stimulated with CD19/HVEM double positive cell line. T cells co-electroporated with both CD19z and BTLA-CD28 CCR RNAs produced higher IFN-gamma than CD19z or CD19-28z electroporated T cells, when stimulated with CD19/HVEM double positive cell line, or CD19 positive K562 that expresses low levels of HVEM (FIG. 2C). The results presented herein demonstrate that BTLA inhibitory signals could be converted to CD28 signals through BTLA-CD28 CCR.

Figure 3B:
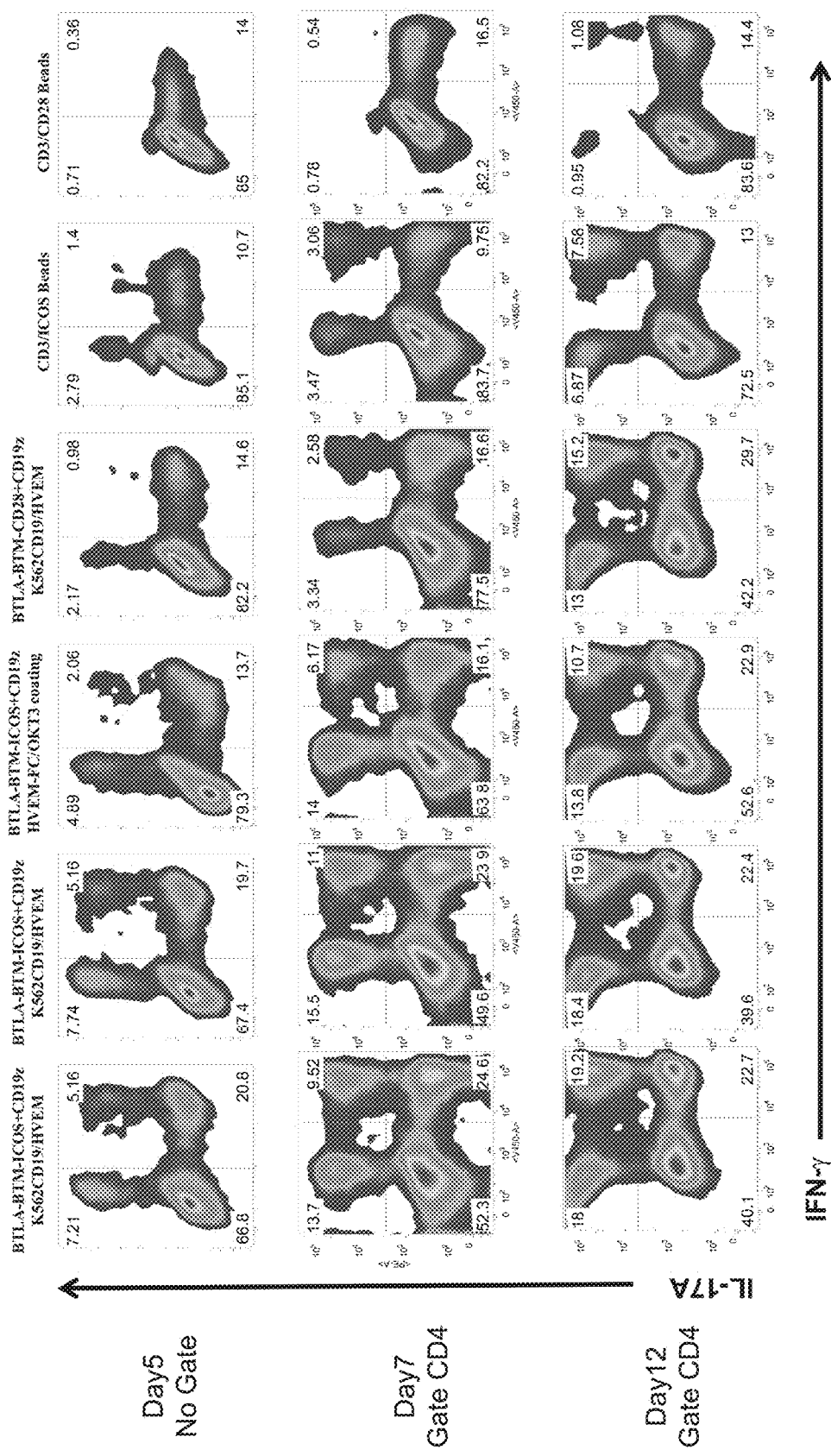

The next set of experiments was designed to test if the inhibitory BTLA signal could be converted to a costimulatory ICOS signal though BTLA-ICOS CCR. Briefly, converting BTLA to ICOS signal was tested in a Th17 polarization system as shown in FIG. 3A. Resting CD4 T cells were co-electroporated with CD19z and BTLA CCRs as indicated (Treatment) and stimulated with CD19/HVEM double positive cell line (Group 1 and 2, duplicates), or T cells were electroporated with BTLA-ICOS alone and stimulated with plate bound HVEM-Fc and OKT3 (group 3). CD3/ICOS beads or CD3/CD28 beads were used as positive and negative controls respectively as described (2010, Paulos et al., Science Translational Medicine). All cultures were conducted in the presence of a Th17 cytokine cocktail. On different days (as indicated) post stimulation, the T cells were stimulated with PMA/Ionomycin and IL-17A and IFN-gamma was detected by intracellular cytokine staining (FIG. 3B). The results showed that ICOS signal converted from BTLA-ICOS enhanced Th17 cell production in the presence of HVEM inhibitory signals.

Converting PD-1 to CD28 Signals

To test whether ligation of PD1 CCR expressed on the T cells surface could be expressed functionally to transduce signals through CD28 or CD27 or ICOS intracellular domain, IVT RNAs encoding PD1 CCR were used (sequences shown below).

Figure 4A:
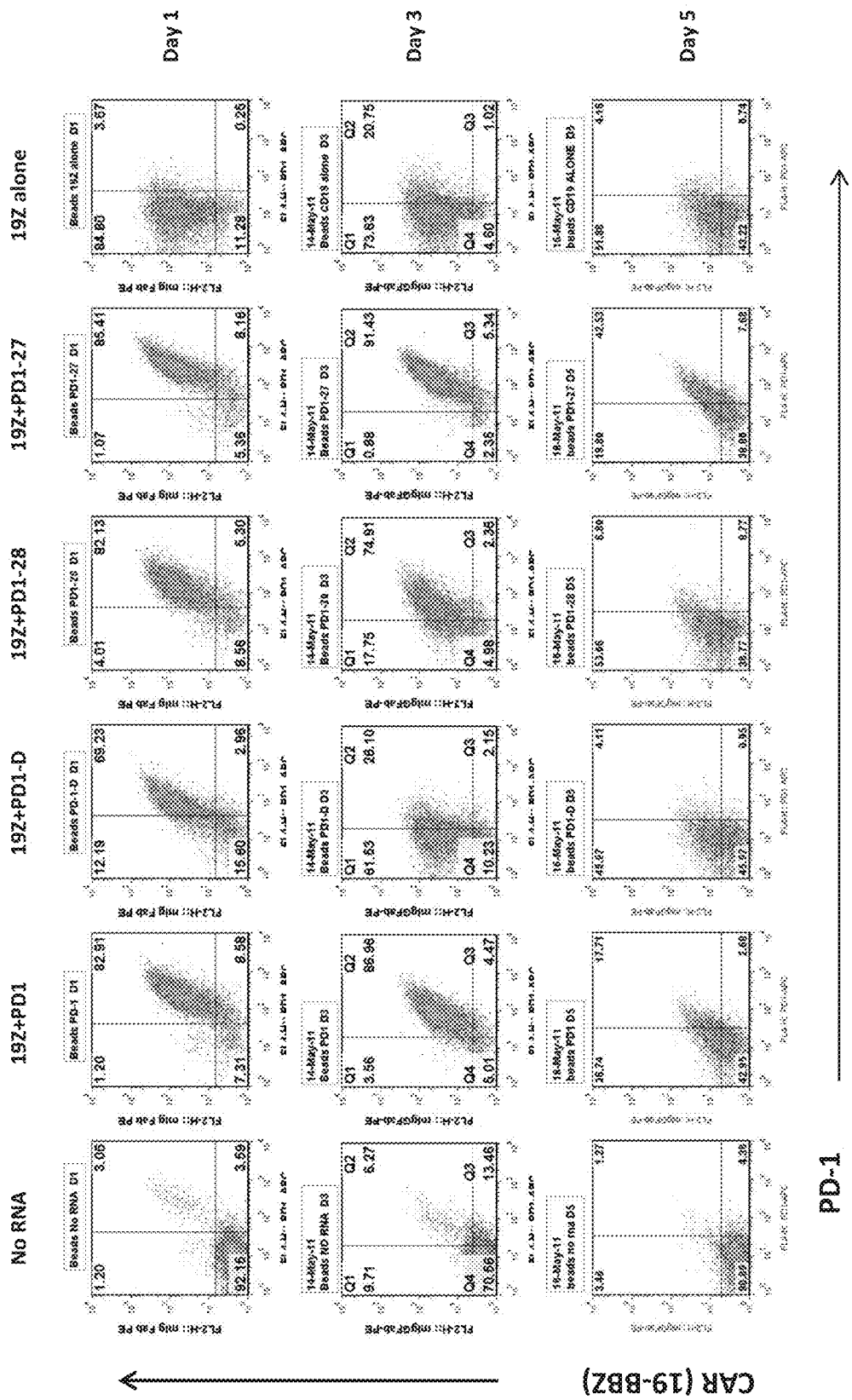
FIGS. 4A through 4D, is a series of images demonstrating that PD1 signals can be converted to CD28 signals.
Figure 4B:
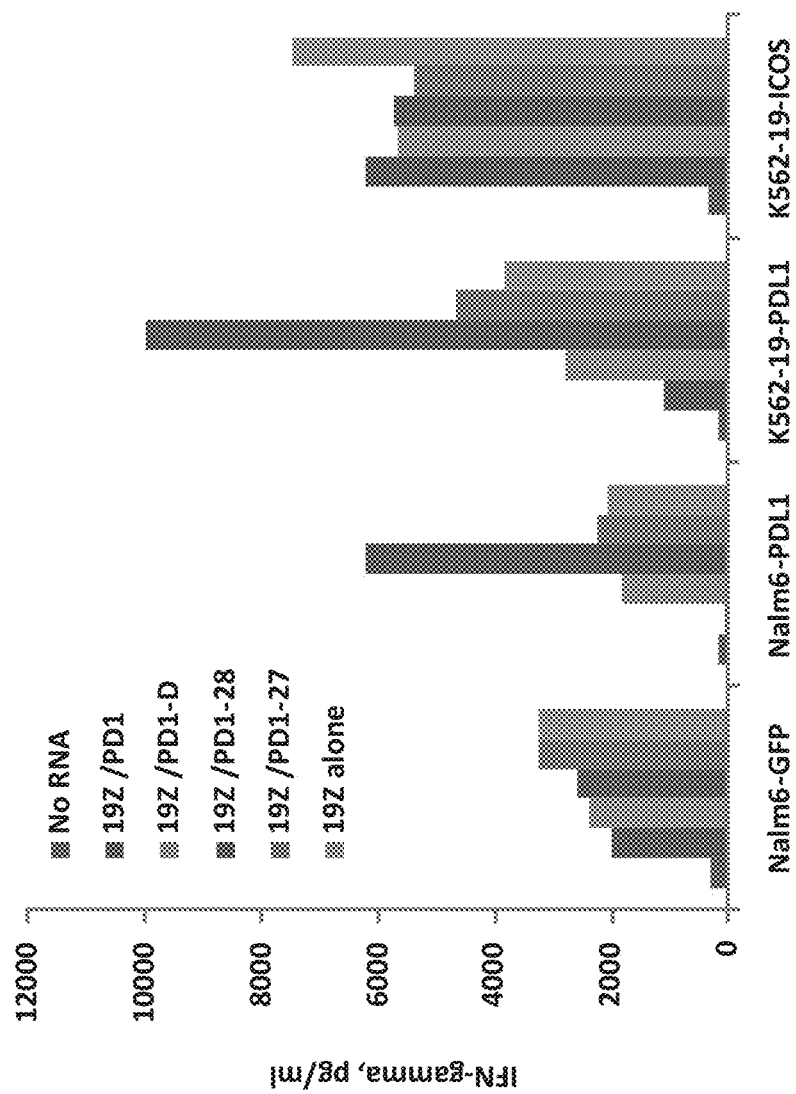

PD1-I-ICOS;
SEQ ID NO. 10
Atgcagatcccacaggcgccctggccagtcgtctgggcggtgctacaact gggctggcggccaggatggttcttagactccccagacaggccctggaacc ccccaccttctccccagccctgctcgtggtgaccgaaggggacaacgcc accttcacctgcagcttctccaacacatcggagagcttcgtgctaaactg gtaccgcatgagccccagcaaccagacggacaagctggccgccttccccg aggaccgcagccagcccggccaggactgccgcttccgtgtcacacaactg cccaacgggcgtgacttccacatgagcgtggtcagggcccggcgcaatga cagcggcacctacctctgtggggccatctccctggcccccaaggcgcaga tcaaagagagcctgcgggcagagctcagggtgacagagagaagggcagaa gtgcccacagcccaccccagcccctcacccaggccagccggccagttcca aaccctggtgttctggttacccataggatgtgcagcctttgttgtagtct gcatttggatgcatacttatttgttggcttacaaaaaagaagtattca tccagtgtgcacgaccctaacggtgaatacatgttcatgagagcagtgaa cacagccaaaaaatctagactcacagatgtgaccctataa PD1-28-CD28;
SEQ ID NO. 11
Atgcagatcccacaggcgccctggccagtcgtctgggcggtgctacaact gggctggcggccaggatggttcttagactccccagacaggccctggaacc ccccaccttctccccagccctgctcgtggtgaccgaaggggacaacgcc accttcacctgcagcttctccaacacatcggagagcttcgtgctaaactg gtaccgcatgagccccagcaaccagacggacaagctggccgccttccccg aggaccgcagccagcccggccaggactgccgcttccgtgtcacacaactg cccaacgggcgtgacttccacatgagcgtggtcagggcccggcgcaatga cagcggcacctacctctgtggggccatctccctggcccccaaggcgcaga tcaaagagagcctgcgggcagagctcagggtgacagagagaagggcagaa gtgcccacagcccaccccagcccctcacccaggccagccggccagttcca aaccctggtgtttgggtgctggtggtggttggtggagtcctggcttgct atagcttgctagtaacagtggcctttattattttctgggtgaggagtaag aggagcaggctcctgcacagtgactacatgaacatgactccccgccgccc cgggcccacccgcaagcattaccagccctatgccccaccacgcgacttcg cagcctatcgctcctaa PD1-CD27;
SEQ ID NO. 12
Atgcagatcccacaggcgccctggccagtcgtctgggcggtgctacaact gggctggcggccaggatggttcttagactccccagacaggccctggaacc ccccaccttctccccagccctgctcgtggtgaccgaaggggacaacgcc accttcacctgcagcttctccaacacatcggagagcttcgtgctaaactg gtaccgcatgagccccagcaaccagacggacaagctggccgccttccccg aggaccgcagccagcccggccaggactgccgcttccgtgtcacacaactg cccaacgggcgtgacttccacatgagcgtggtcagggcccggcgcaatga cagcggcacctacctctgtggggccatctccctggcccccaaggcgcaga tcaaagagagcctgcgggcagagctcagggtgacagagagaagggcagaa gtgcccacagcccaccccagcccctcacccaggccagccggccagttcca aaccctggtgatcttgtgatcttctctggaatgttccttgttttcaccc tggccggggccctgttcctccatcaacgaaggaaatatagatcaaacaaa ggagaaagtcctgtggagcctgcagagccttgtcgttacagctgccccag ggaggaggagggcagcaccatccccatccaggaggattaccgaaaaccgg agcctgcctgctcccccctaa PD1 CCR as indicated and CD19z RNA were co-electroporated into stimulated T cells and the transgenes were detected by anti-PD1 and anti-CAR Abs at the time points as indicated (FIG. 4A). Co-electroporated T cells as described in FIG. 4A were co-cultured with Nalm6 (human B cell leukemia line) expressing PD-L1 or GFP as control, or K562-CD19 expressing PD-L1, or ICOSL as control. IFN-gamma production was assayed 24 h after co-culture. T cells co-introduced with CD19z and PD1-CD28 (PD1-28) showed significantly higher IFN-gamma production than T cells electroporated with CD19z alone, or co-electroporated with PD1 with cytoplasmic domain being truncated, or PD1-CD27 (PD1-27). When co-cultured with CD19/PD-L1 double positive cell lines. Strong T cell inhibition was seen when T cells were co-electroporated with CD19z and full length (wild type) PD1 and stimulated with CD19/PD-L1 double positive cell lines (FIG. 4B).

Figure 4C:
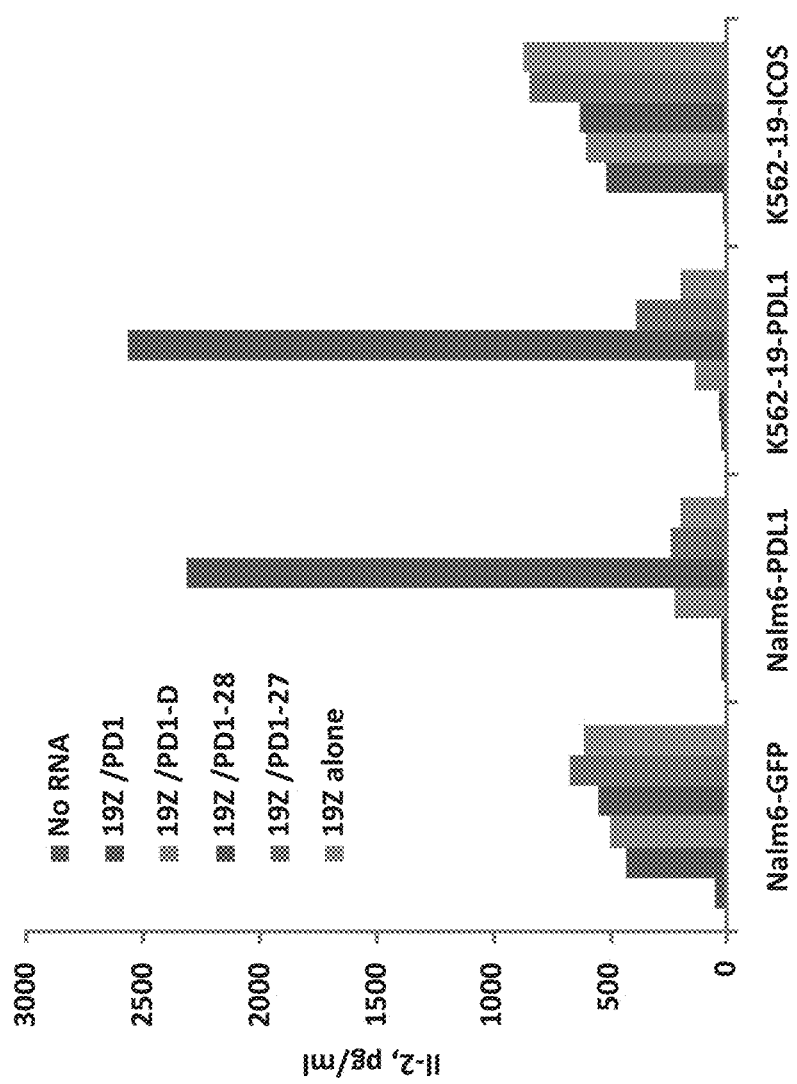
Figure 4D:
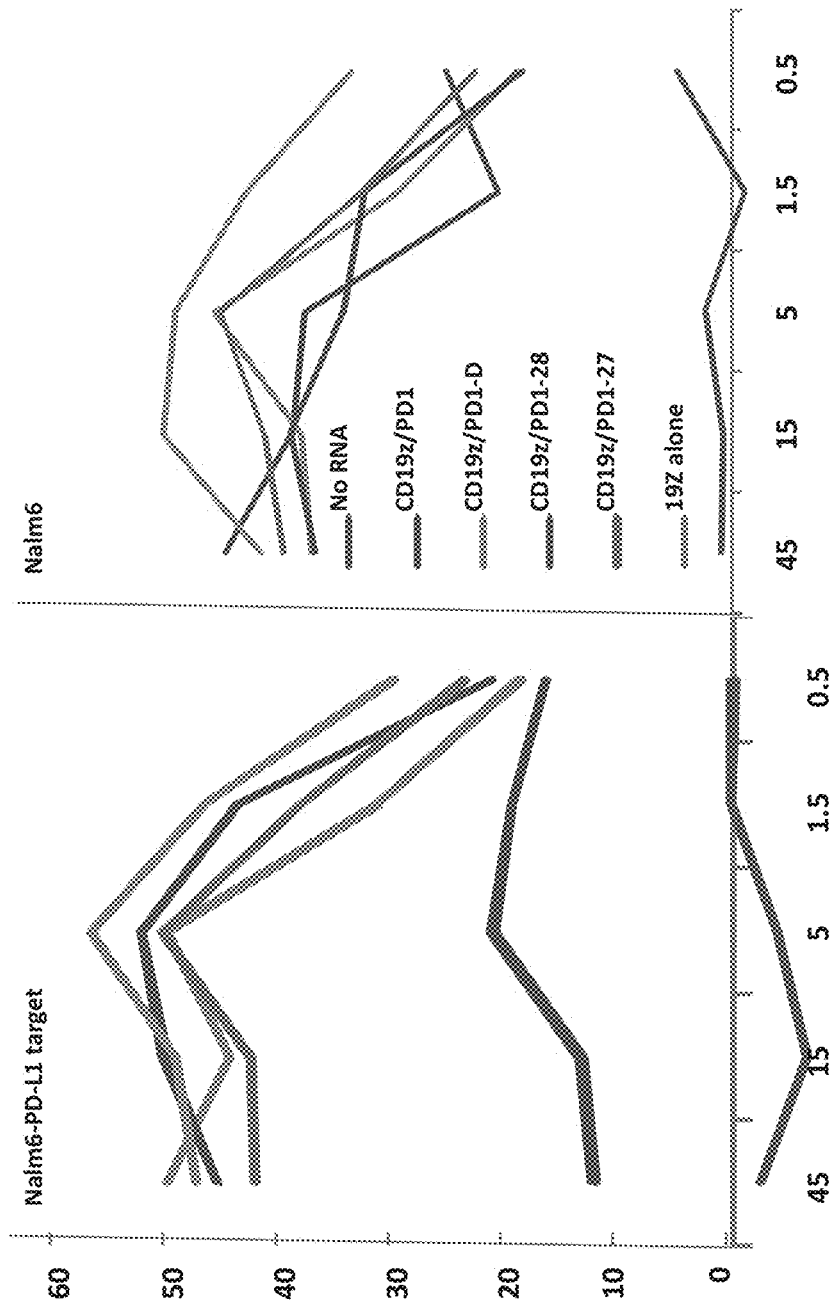

Co-electroporated T cells as described in FIG. 4A were co-cultured with Nalm6 (human B cell leukemia line) expressing PD-L1 or GFP as control, or K562-CD19 expressing PD-L1, or ICOSL as control. IL-2 production was assayed 24 h after co-culture. T cells co-introduced with CD19z and PD1-CD28 (PD1-28) showed significantly higher IL-2 production than T cells electroporated with CD19z alone, or co-electroporated with PD1 with cytoplasmic domain being truncated, or PD1-CD27 (PD1-27). When co-cultured with CD19/PD-L1 double positive cell lines, strong T cell inhibition was seen when T cells co-electroporated with CD19z and full length PD1 and stimulated with CD19/PD-L1 double positive cell lines (FIG. 4C).

Co-electroporated T cells as described in FIG. 4A were tested in a flow based CTL assay. T cells co-introduced with CD19z and PD1 showed significantly reduced killing ability against Nalm6-PD-L1 targets, while no significant differences were seen for T cells co-electroporated with PD1 CCRs compared to T cells electroporated with CD19Z alone, when using Nalm6-PD1 as target. When PD1 ligand negative Nalm6 was used as target, no significant differences were found for all T cell groups, including T cells co-electroporated with CD19z and PD1.

The next set of experiments was designed to reverse PD1 inhibition by PD1-CD28 CCR co-introduction. To mimic that of the tumor microenvironment or under chronic infection where the T cells are PD1 positive, T cells were stimulated with CD3/CD28 beads or OKT3/PBMC/IL2 and were co-electroporated with CD19z (10 ug) and PD1 (5 ug) with additional PD1 CCR (10 ug) as indicated. CAR and PD1 and/or PD1 CCR expression were detected by FACS one day post electroporation (FIG. 5A).

Figure 5A:
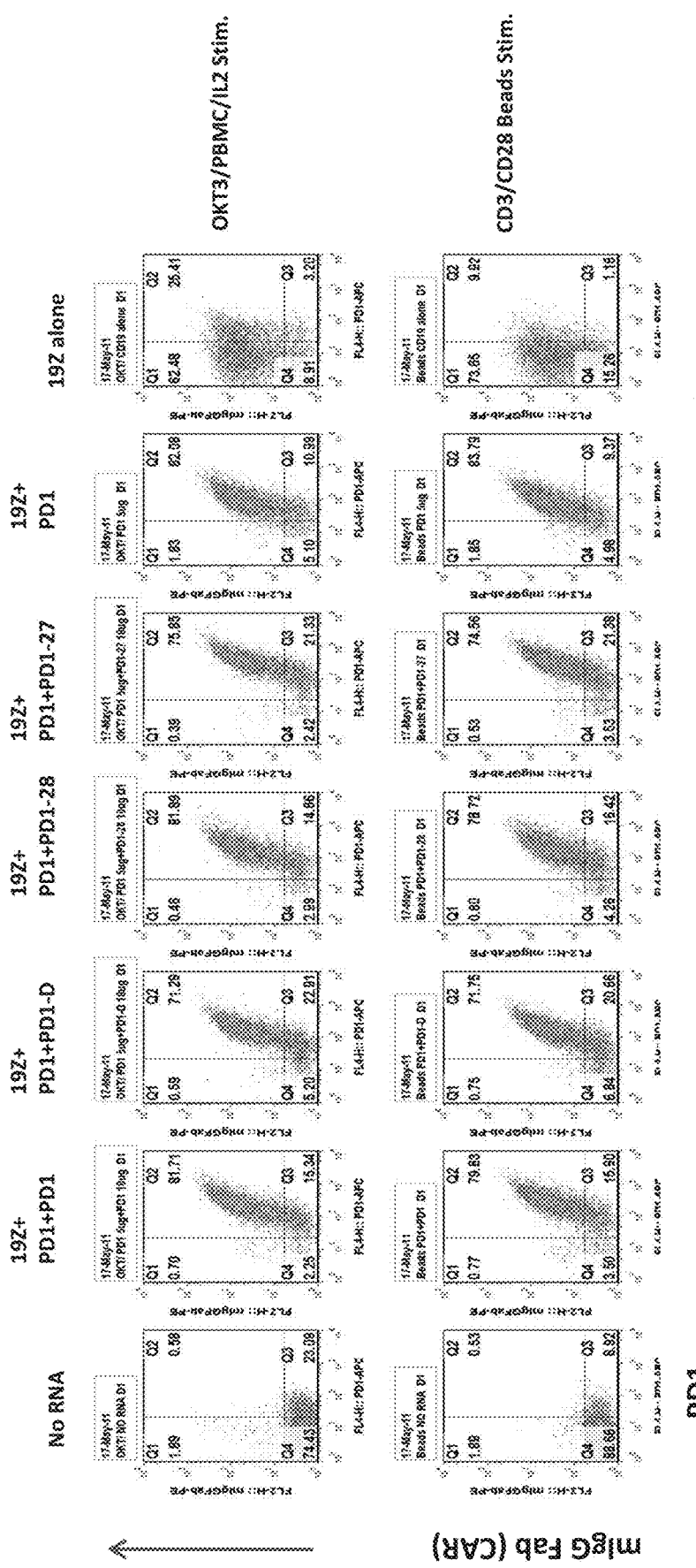
FIGS. 5A and 5C, is a series of images demonstrating reversal of PD1 inhibition by PD1-CD28 CCR co-introduction.
Figure 5B:
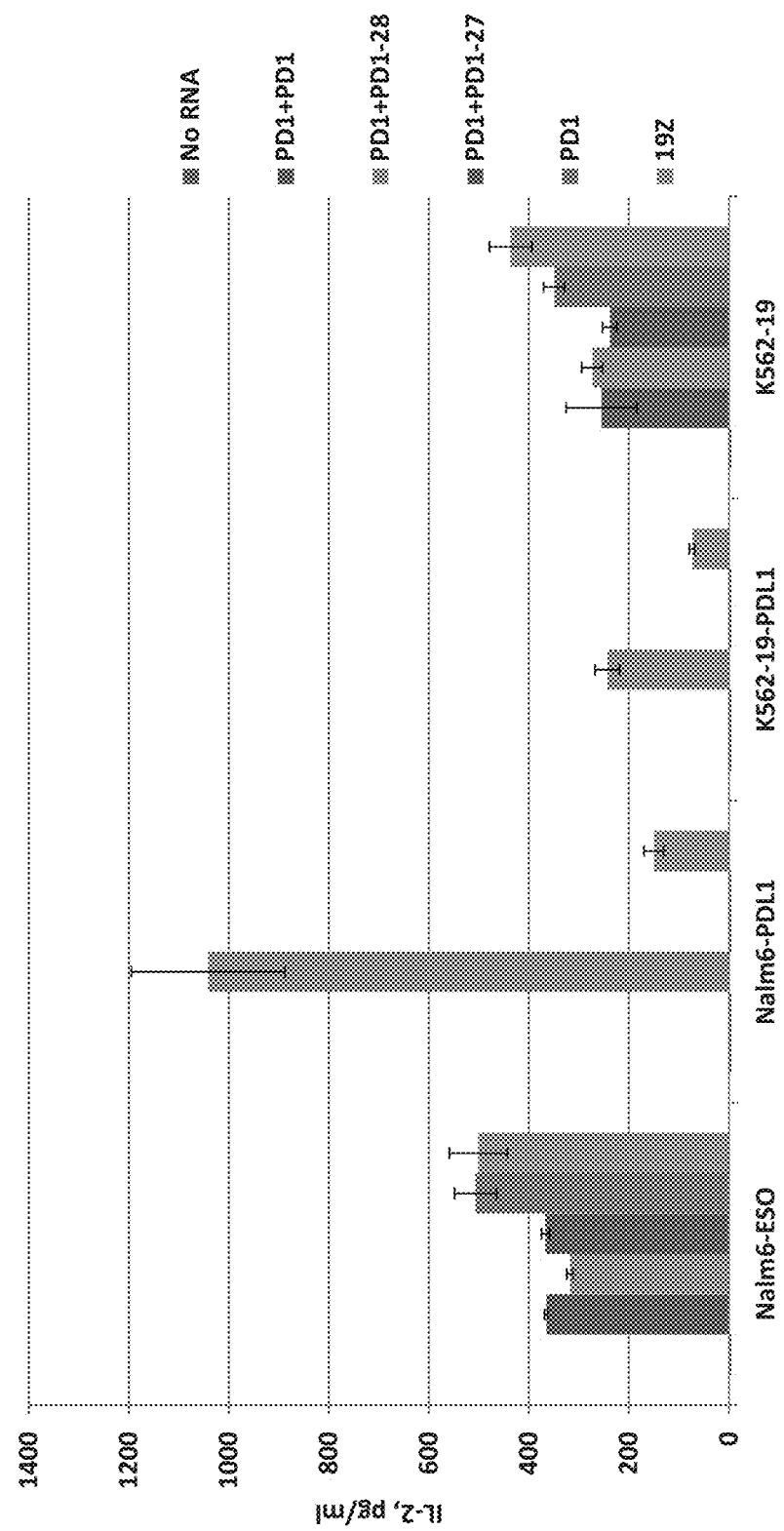
FIG. 5, comprising

T cells electroporated as shown in FIG. 5A were co-cultured with Nalm6 or K562-CD19 expressing PD-L1. IL-2 production was assayed after overnight co-culture. The results showed that there was a decreased amount of IL-2 produced by T cells electroporated with CD19z alone, compared with the same T cells co-cultured with CD19 positive cell lines without PD-L1. However, in the presence of PD1, the IL-2 production was completely blocked when co-cultured with PD-L1 positive cell lines, except the T cells co-electroporated with PD1-CD28 (PD1-28), which showed much higher IL-2 production than CD19Z alone T cells, while PD1 expression on the T cells had minimum influence on T cells when the T cells were co-cultured with PD-L1 negative cell lines (FIG. 5B).

Figure 5C:
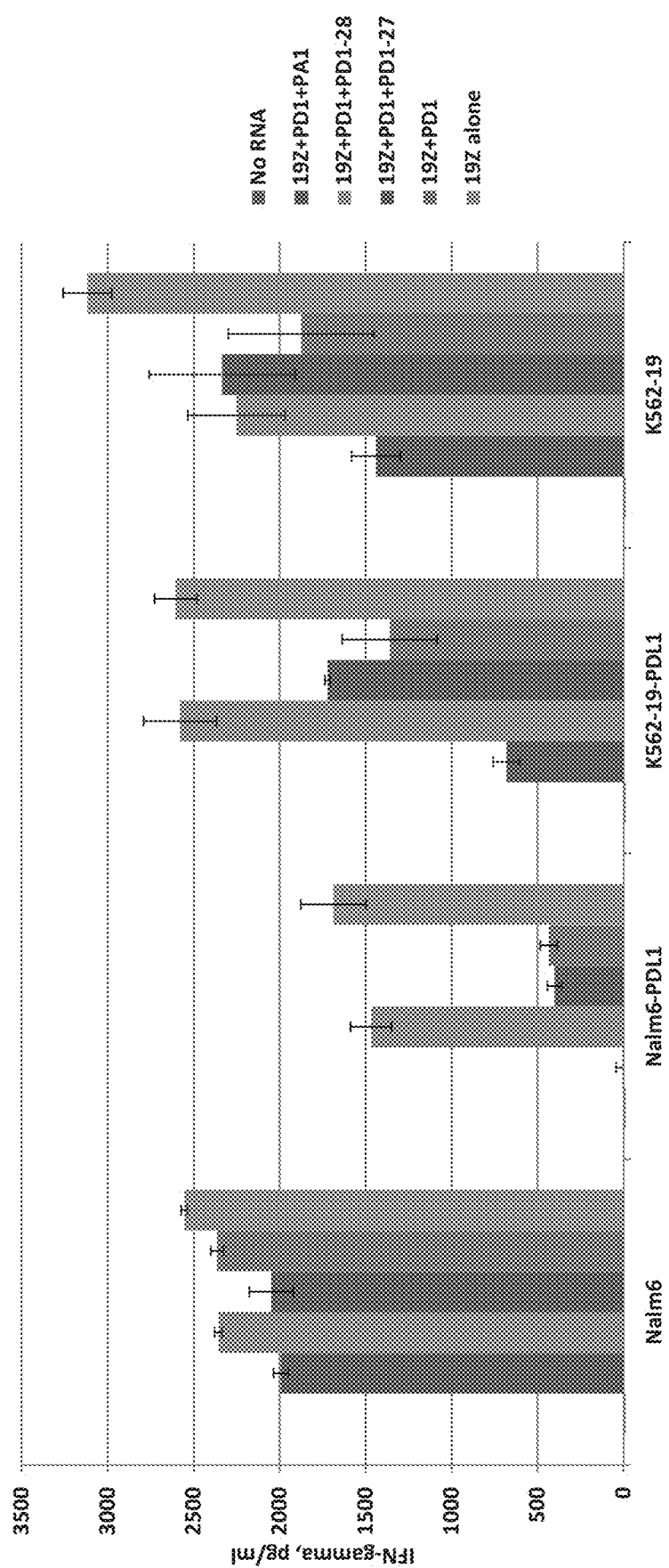

T cells electroporated as shown in FIG. 5A were co-cultured with Nalm6 or K562-CD19 expressing PD-L1. IFN-gamma production was assayed after overnight co-culture (FIG. 5C). A similar cytokine production profile was seen as that of IL-2 production shown in FIG. 5B. The results presented herein demonstrate that PD1-CD28 CCR can reverse the inhibitory effect of PD1 and promote T cell effector functions.

Converting PD1 to ICOS Signals

Figure 6A:
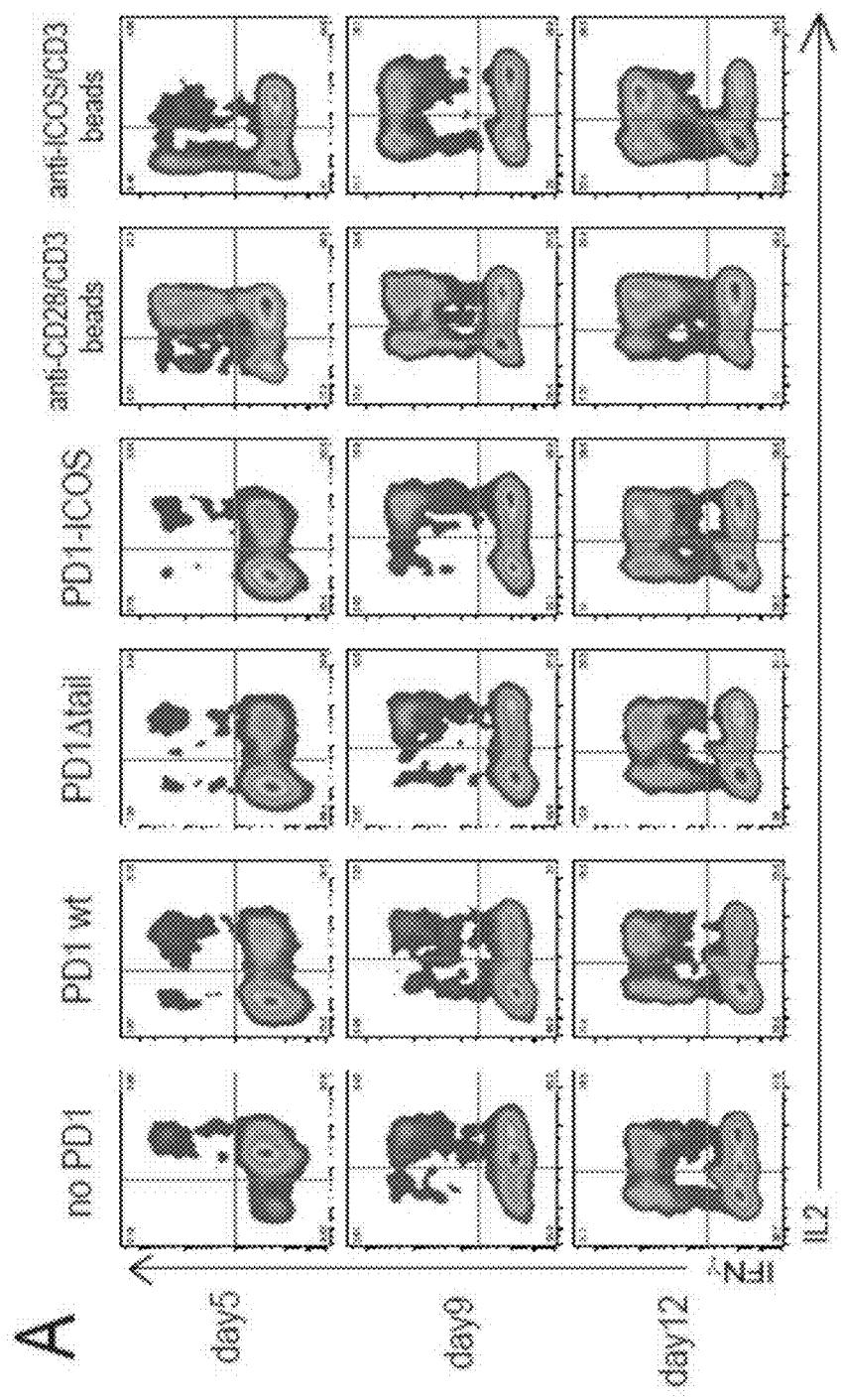
FIGS. 6A through 6C, is a series of images demonstrating conversion of PD1 signal into ICOS signal.
Figure 6B:
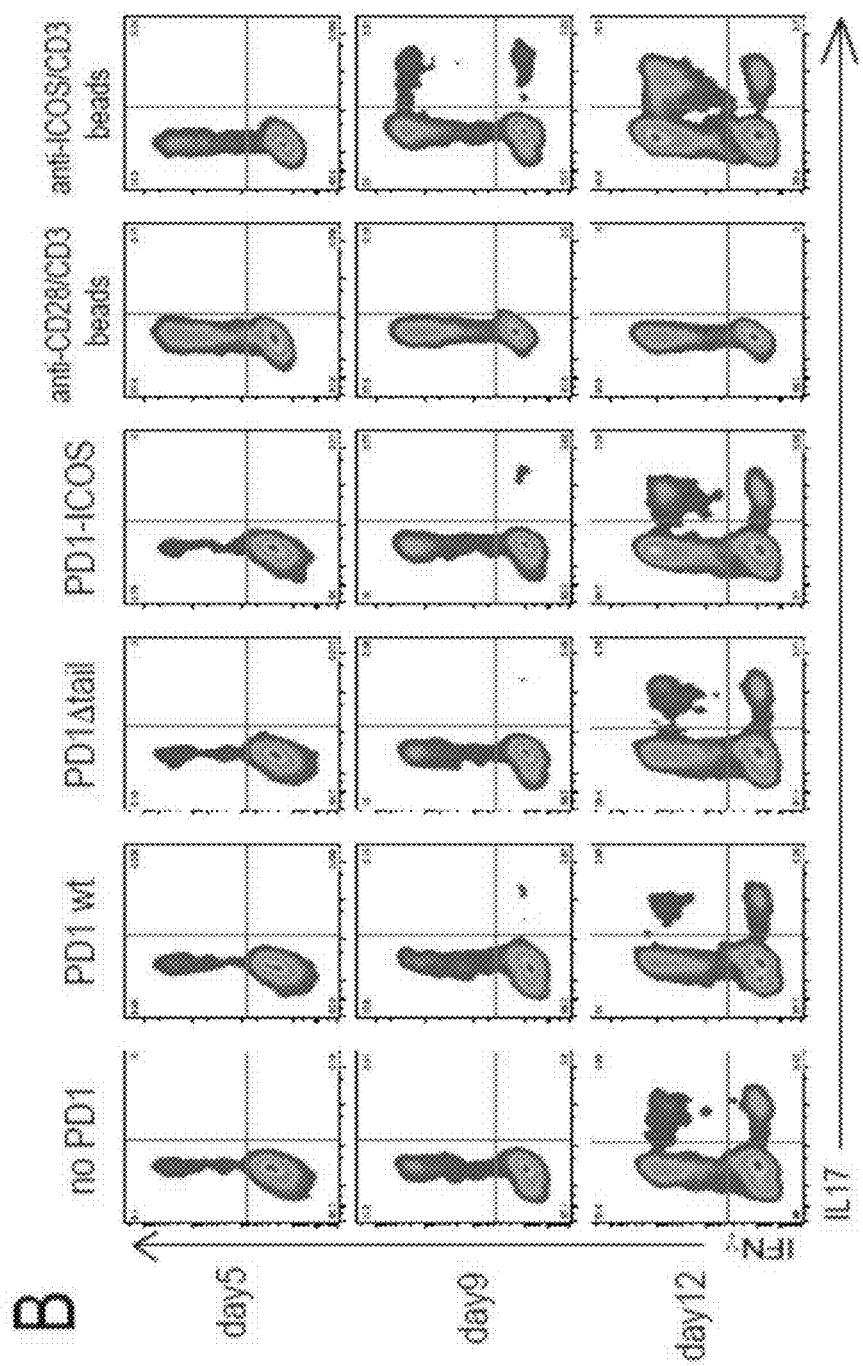
Figure 6C:
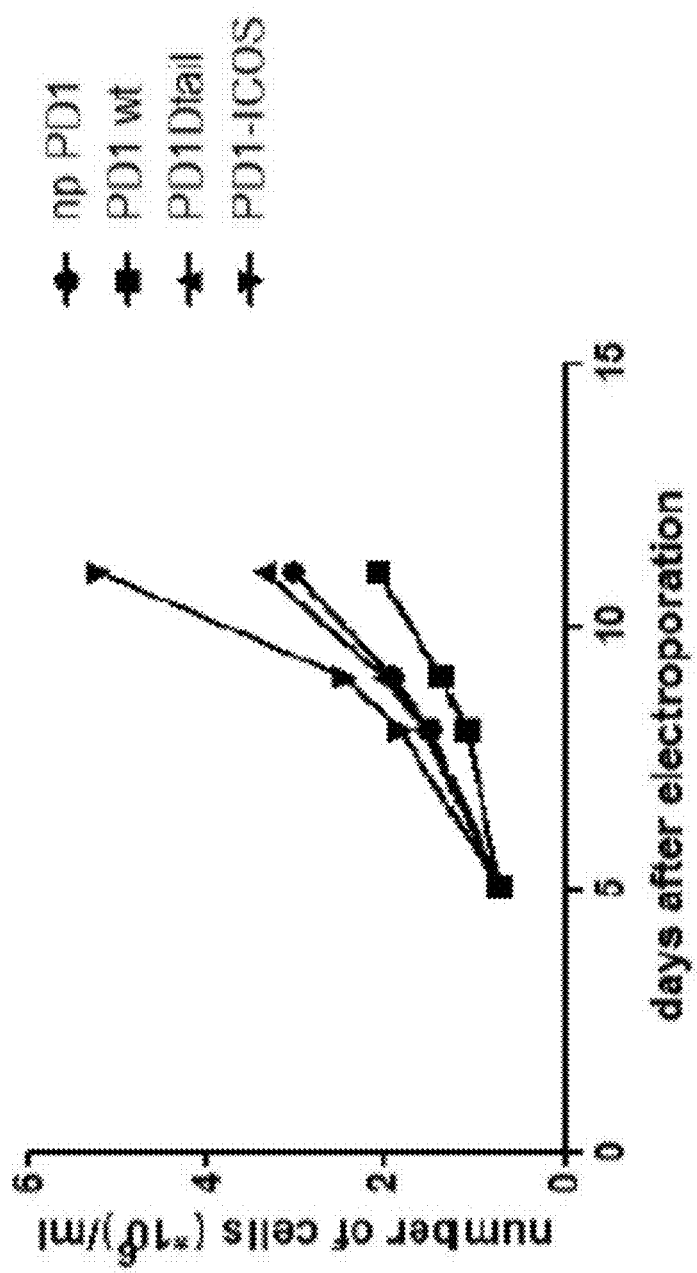

CD4 T cells were electroporated with PD1 (or PD1 variants) and CD19-z CAR mRNA (10 ug each). 4 hours after electroporation (day0), T cells were mixed with K562 cells (0.5:1=K562:T cell) expressing PD-L1 and CD19 in R10 culture media in the presence of IL1 (10 ng/ml), IL6 (10 ng/ml), IL23 (20 ng/ml), and neutralizing antibodies (10 µg/ml) against IL4 and IFNγ. At indicated days (5, 9, and 12 days after electroporation) cells were incubated for 4 hours with PMA (3 ug/ml) and ionomycin (1 ug/ml) and GolgiStop for intracellular cytokine staining. Surface staining for CD4 was performed, followed by intracellular staining for IFN-gamma, IL17 and IL2. CD4 T cells stimulated with anti-CD28/CD3 beads and anti-ICOS/CD3 beads were used as controls (FIG. 6A). Cytokine production was enhanced, particularly at day 9 in cells expressing PD1-ICOS compared to PD1 wild type or tailess PD1. Cellular proliferation of stimulated T cells is shown in FIG. 6C.

PD-1 Chimeric Receptors

PD-1 is upregulated on the surface of exhausted CD8 T cells in patients with chronic viral infection. Blocking the PD-1:PD-L1 signal restores the function of PD-1 expressing exhausted CD8 T cells. Many tumors express PD-L1 providing a immunosuppressive microenvironment.

The purpose of the following experiments is to direct adoptively transferred T cells to overcome the inhibitory tumor microenvironment by introducing PD-1 chimeric receptors to the tumor site.

Figure 7:
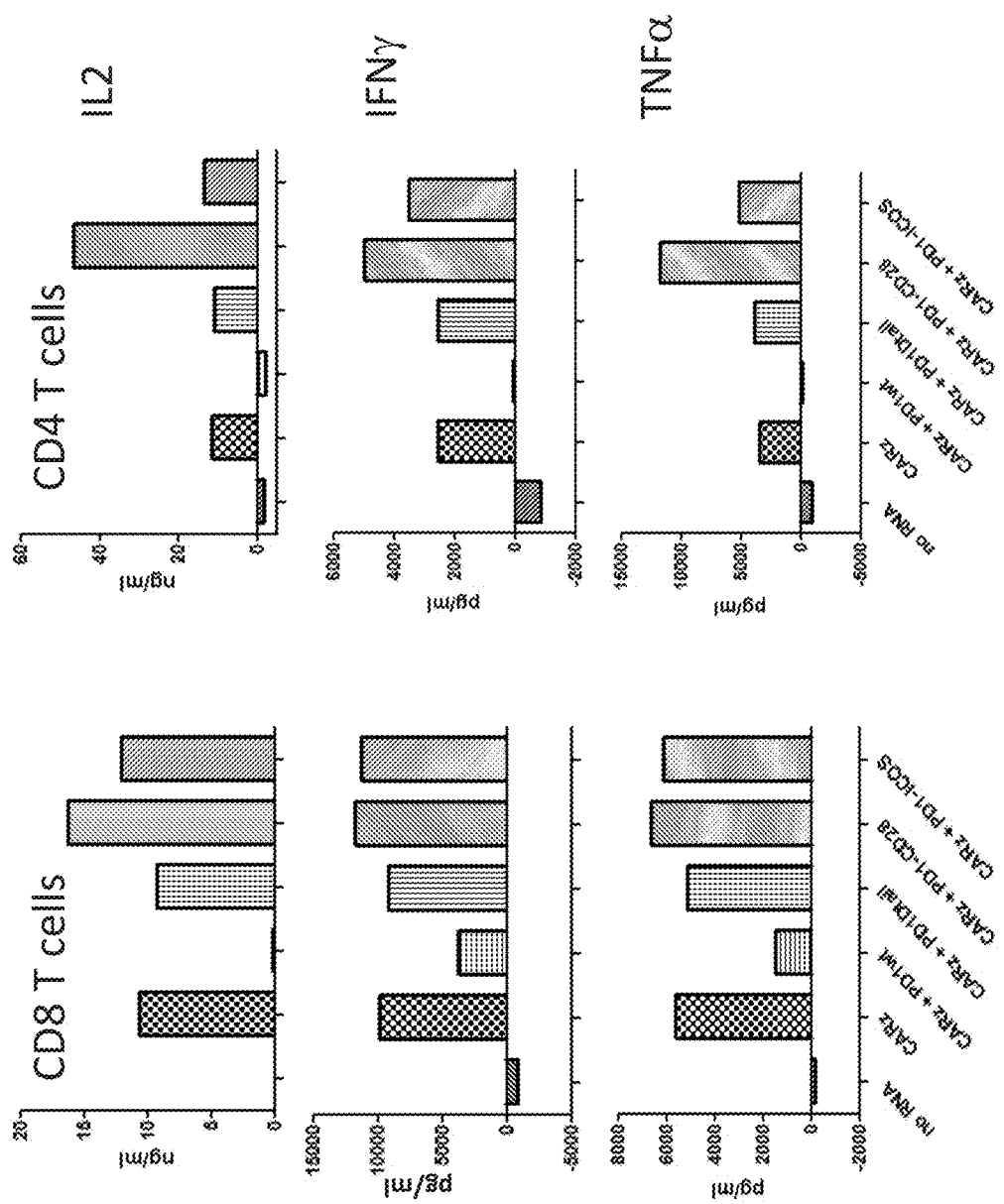
FIG. 7 is an image demonstrating that the inhibitory effect of PD1 wt on cytokine production is rescued by PD1 chimeric constructs.
Figure 8:
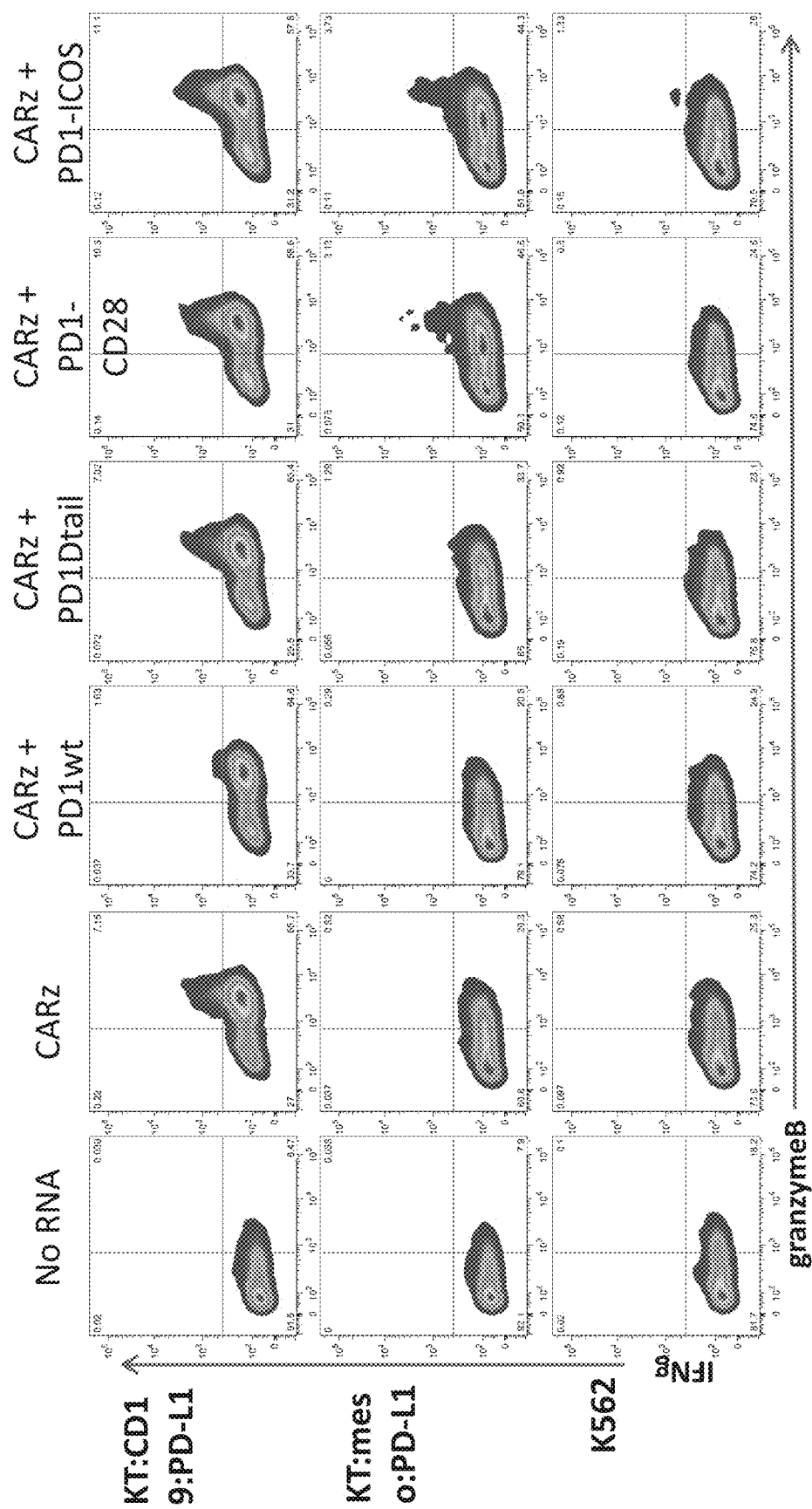
FIG. 8 is an image demonstrating that PD-1 chimeric receptors do not affect granzymeB production.
Figure 9:
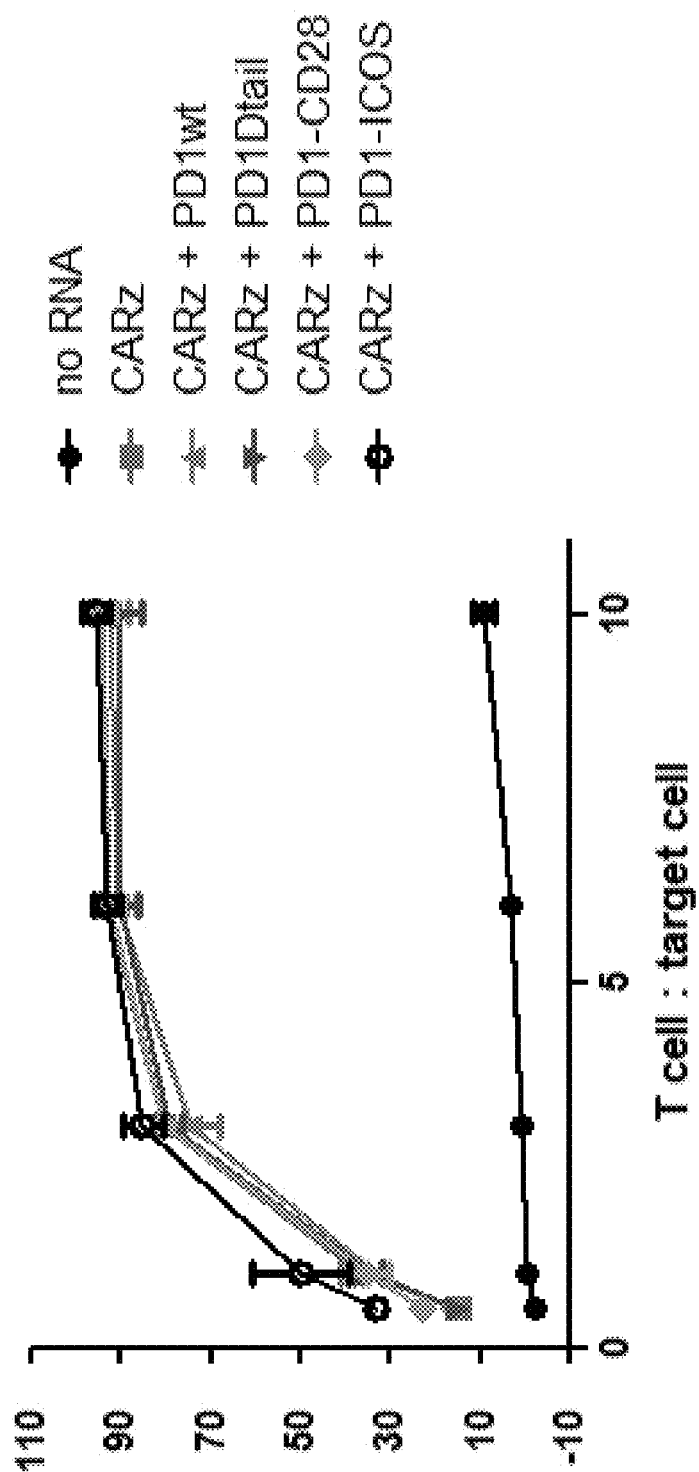
FIG. 9 is an image demonstrating that minimal differences were observed in the killing activity of CD8 T cells in the presence or absence of PD1.

It was observed that the inhibitory effect of PD1wt on cytokine production is rescued by PD1 chimeric constructs (FIG. 7). However, PD1 chimeric receptors do not affect granzyme B production (FIG. 8). Similarly, minimal differences were observed in the killing activity of CD8 T cells in the presence or absence of PD1 (FIG. 9).

Figure 10:
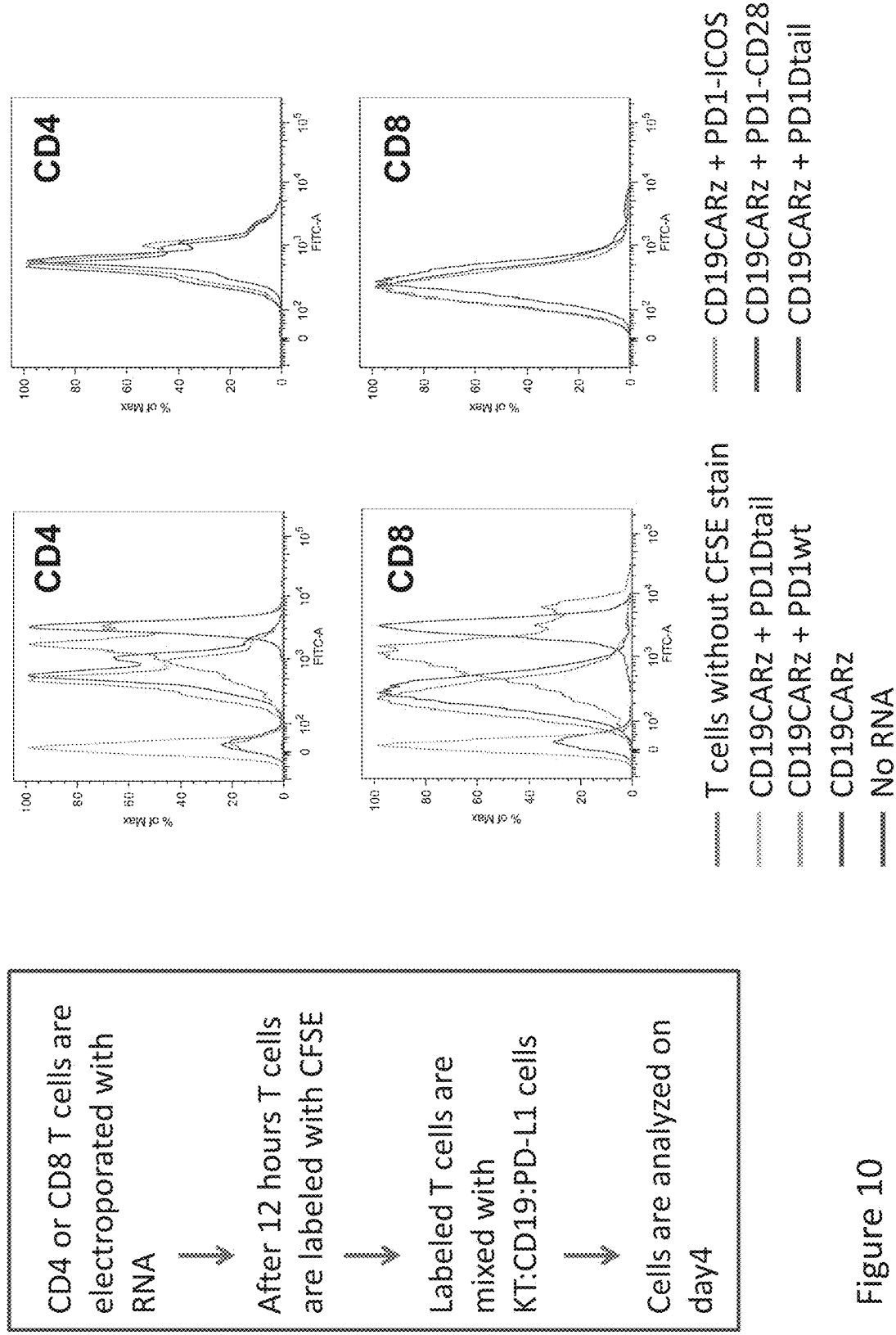
FIG. 10 is an image showing the effect of PD-1 chimeric receptors on T cell proliferation.
Figure 11:
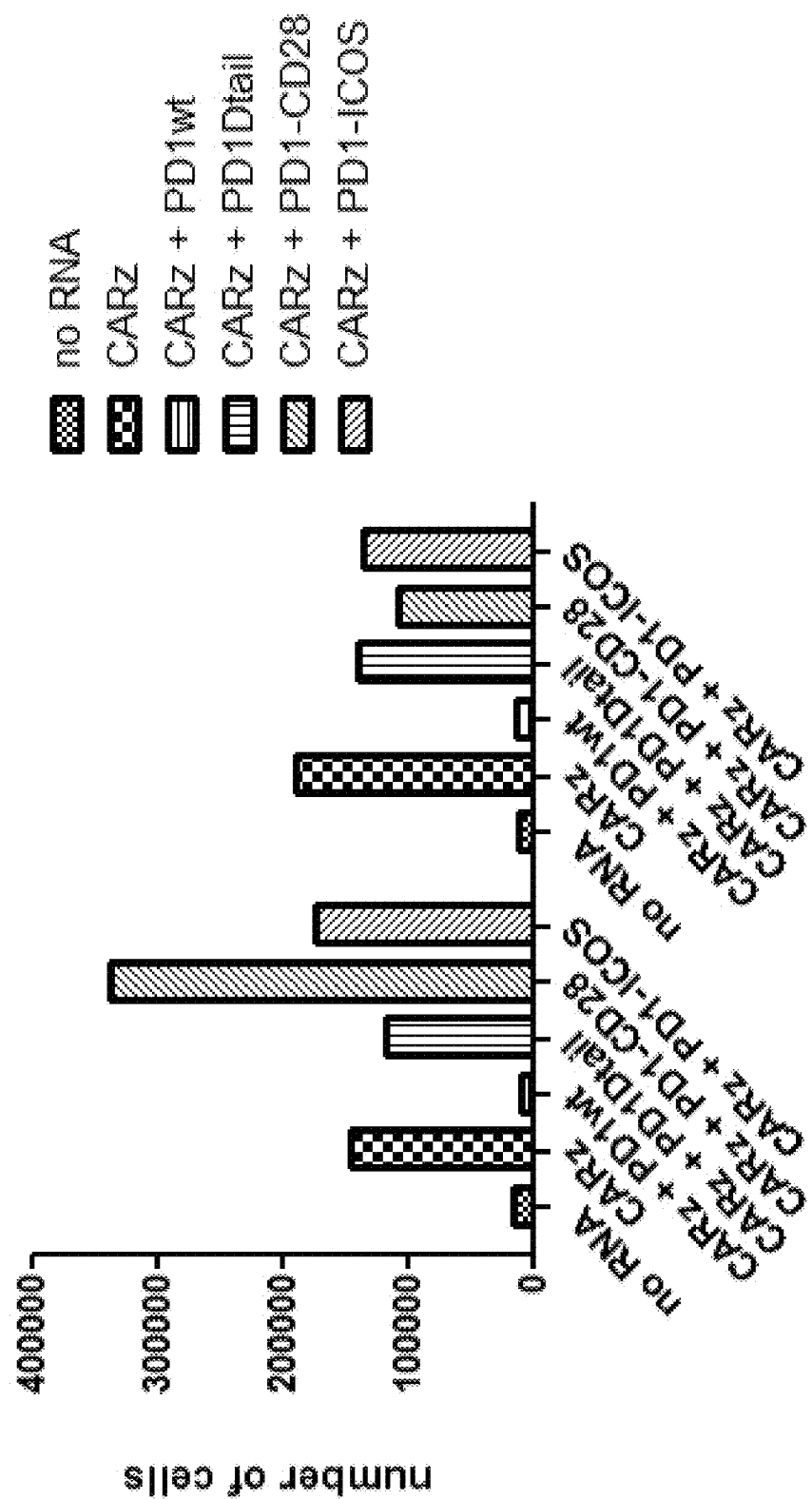
FIG. 11 is an image showing that PD1-CD28 chimeric receptor increases the number of CD8 T cells.

The next set of experiments was designed to evaluate the effect of PD-1 chimeric receptors on T cell proliferation (FIG. 10). It was observed that PD1-CD28 chimeric receptor increases the number of CD8 T cells (FIG. 11).

In summary, the results presented herein demonstrate that PD-1 chimeric constructs do not exhibit the inhibitory effects shown by PD-1 wt. PD1-CD28 seems to augment the production of TNFα, IL2 and IFNγ in CD4 T cells. PD-1 chimeric receptors did not show increased cytotoxicity above that of T cells expressing CD19CARz itself. PD1-CD28 increased CD8 T cell numbers above that of T cells expressing CD19CARz itself.

Redirecting Co-Inhibitory Signaling to Positive Co-Stimulation

The results presented herein demonstrate that switch receptors were expressed in T cells by electroporation, or with lentiviral vectors. It was observed that CARs and switch receptors can be expressed in the same T cell. When the cells expressing CARs or TCRs and switch receptor are exposed to tumor cells that have ligands for BTLA or PD-1, the T cells are shown to have a positive immune response, rather than the usual inhibitory response.

When these chimeric receptors are expressed in T cells, in the case of the BTLA switch receptor, upon interaction with their natural ligand HVEM on the tumor cells, it was observed that the T cells were stimulated and then expressed functions associated with positive antitumor effects, including the secretion of IFN-gamma.

Another important result from these studies is that the HVEM:BTLA interaction with the chimeric receptor led to enhanced IL-17 secretion. This is a marker of TH17 cells, a cell that is known to be useful for tumor immunotherapy (Martin-Orozco et al., 2009, Immunity 31:787-98; Paulos et al., 2010, Science Translational Medicine 2:55-78; Garaude et al., 2010, Sci Transl Med 2(55):55ps2). For example, the results presented herein demonstrate that the T cells expressing CARs and BTLA switch receptors with ICOS signaling domains were polarized to secrete large amounts of IL-17.

In addition, the results presented herein show that the T cells expressing CARs and PD1 switch receptors with CD28, and deleted domains were prevented from having inhibition and instead killed tumor cells and secrete cytokines (IL-2 and IFN-gamma) if they expressed PD-1 switch receptors.

Without wishing to be bound by any particular theory, it is believed that by expressing chimeric antigen receptors (CARs) with PD-I or BTLA switch receptors on T cells that are then introduced into the tumor microenvironment, the T cells have an enhanced antitumor effect and display the THI 7 phenotype. The type of adoptive T cell transfer for tumor immunotherapy of the invention is also applicable in the area of vaccine therapy, such as for chronic viral infections including HIV or other viruses such as EBV, HCV or CMV. This technology could be easily incorporated into other trials that are currently using genetically modified T cells with TCRs as well. For example, the switch receptors of the invention can be used in the context of T cells with TCRs specific for cancer antigens such MAGE-A3 and NY-ESO-1, and it is believed that the inclusion of the switch receptors with these T cells would increase the potency of the T cells.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified immune cell engineered to express:
(a) a fusion protein comprising an extracellular domain, a transmembrane domain, and an intracellular domain, wherein:
    (i) the extracellular domain is an extracellular domain of an inhibitory polypeptide that is associated with a negative signal, and wherein the inhibitory polypeptide that is associated with a negative signal is selected from the group consisting of PD-1 and BTLA; and
    (ii) the intracellular domain is an intracellular domain of a stimulatory polypeptide that is associated with a positive signal that activates immune cells, and wherein the stimulatory polypeptide that is associated with a positive signal is selected from the group consisting of CD28 and ICOS; and
(b) a chimeric antigen receptor (CAR) comprising an antigen recognition domain that specifically targets a cancer antigen and an intracellular domain of a CD3-zeta chain;

wherein, when the fusion protein and the CAR are bound to their respective ligands, IL-2 and IFN-γ secretion is enhanced at least three times as compared to IL-2 and IFN-γ secretion in (i) a modified immune cell only expressing the CAR or (ii) a modified immune cell expressing a CAR comprising the antigen recognition domain that specifically targets a cancer antigen, a costimulatory domain, and an intracellular domain of a CD3-zeta chain; and wherein the modified immune cell is polarized to secrete IL-17 and IFN-γ, and wherein the modified immune cell is a modified T cell.

2. The modified immune cell of claim 1, wherein the fusion protein is encoded by a nucleic acid sequence selected from the group consisting of SEQ ID NOs: 2, 4, 6-9 and 10-11.

3. The modified immune cell of claim 2, wherein the modified immune cell is autologous.

4. The modified immune cell of claim 1, wherein the polypeptide that is associated with a negative signal is BTLA.

5. The modified immune cell of claim 1, wherein the polypeptide that is associated with a negative signal is PD-1.

6. The modified immune cell of claim 1, wherein the polypeptide that is associated with a positive signal is CD28.

7. The modified immune cell of claim 1, wherein the polypeptide that is associated with a positive signal is ICOS.

8. The modified immune cell of claim 1, wherein the transmembrane domain is the transmembrane domain of the inhibitory polypeptide that is associated with the negative signal.

9. The modified immune cell of claim 1, wherein the transmembrane domain is the transmembrane domain of the stimulatory polypeptide that is associated with the positive signal.

10. The modified immune cell of claim 1, wherein the polypeptide that is associated with a negative signal is PD-1, and the polypeptide that is associated with a positive signal is CD28.

11. The modified immune cell of claim 1, wherein the CAR comprises an antigen recognition domain that specifically targets CD19.

12. A population of modified immune cells engineered to express:
    (a) a fusion protein comprising an extracellular domain, a transmembrane domain, and an intracellular domain, wherein the extracellular domain is an extracellular domain of PD-1, and wherein the intracellular domain is an intracellular domain of CD28; and
    (b) a chimeric antigen receptor (CAR) comprising an antigen recognition domain that specifically targets a cancer antigen and an intracellular domain of a CD3-zeta chain; and
    wherein, when the fusion protein and the CAR are bound to their respective ligands, IL-2 and IFN-γ secretion is enhanced at least three times as compared to IL-2 and IFN-γ secretion in modified immune cells only expressing the CAR; and
    wherein the population of modified immune cells comprise modified $CD4^+$ T cells and modified $CD8^+$ T cells, and wherein the fusion protein enhances TNFα, IL2 and IFNγ secretion in $CD4^+$ T cells, thereby enhancing the $CD4^+$ T cells antitumor response.

13. The population of modified immune cell of claim 12, wherein the fusion protein-induced TNFα, IL2 and IFNγ secretion in $CD4^+$ T cells is at least 2-fold higher than the fusion protein-induced TNFα, IL2 and IFNγ secretion in $CD8^+$ T cells.

14. The population of modified immune cell of claim 12, wherein the fusion protein enhances $CD8^+$ T cells proliferation.

15. The population of modified immune cell of claim 12, wherein the CAR comprises an antigen recognition domain that specifically targets CD19.

* * * * *